US010682215B2

(12) United States Patent
Couderc et al.

(10) Patent No.: US 10,682,215 B2
(45) Date of Patent: Jun. 16, 2020

(54) METHOD FOR FORMING A MESH HAVING A BARBED SUTURE ATTACHED THERETO AND THE MESH THUS OBTAINED

(71) Applicant: Sofradim Production, Trévoux (FR)

(72) Inventors: Xavier Couderc, Frans (FR); Pierre Bailly, Caluire et Cuire (FR)

(73) Assignee: Sofradim Production, Trévoux (FR)

( * ) Notice: Subject to any disclaimer, the term of this patent is extended or adjusted under 35 U.S.C. 154(b) by 280 days.

(21) Appl. No.: 15/716,979

(22) Filed: Sep. 27, 2017

(65) Prior Publication Data

US 2018/0110605 A1 Apr. 26, 2018

(30) Foreign Application Priority Data

Oct. 21, 2016 (EP) .................................... 16306383

(51) Int. Cl.
*A61F 2/00* (2006.01)
*D04B 21/12* (2006.01)
*A61B 17/06* (2006.01)

(52) U.S. Cl.
CPC ............ *A61F 2/0063* (2013.01); *D04B 21/12* (2013.01); *A61B 2017/06176* (2013.01); *A61F 2002/0068* (2013.01); *A61F 2220/0016* (2013.01); *A61F 2250/0036* (2013.01); *D10B 2509/04* (2013.01); *D10B 2509/08* (2013.01)

(58) Field of Classification Search
CPC ............................... A61F 2/0063; D04B 21/12
See application file for complete search history.

(56) References Cited

U.S. PATENT DOCUMENTS

| 1,187,158 A | 6/1916 | Mcginley |
| 3,054,406 A | 9/1962 | Usher |
| 3,118,294 A | 1/1964 | Van Laethem |

(Continued)

FOREIGN PATENT DOCUMENTS

| CA | 1317836 C | 5/1993 |
| CN | 201879864 U | 6/2011 |

(Continued)

OTHER PUBLICATIONS

Machine Translation EP 1 382 728 (Year: 2003).*

(Continued)

*Primary Examiner* — Matthew J Daniels
*Assistant Examiner* — Wayne K. Swier

(57) ABSTRACT

The invention relates to a method for forming a mesh having a barbed suture attached thereto, comprising the following steps:
a) producing a knitted structure on a knitting machine comprising at least one needle-bed with three guide bars, on a length corresponding to N stitches ranging from 1 to N, wherein
  i) a first knit portion is produced along stitches ranging from 1 to x, where $1<x<N$,
  ii) a second knit portion is produced for stitches ranging from (x+1) to N, in which the knitting pattern produces at least one weft stitched chain stitch,
b) cutting the second knit portion on both sides of the weft stitched chain stitch and along an edge separating the second knit portion from the first knit portion, while maintaining the weft stitched chain stitch attached to the first knit portion.

The invention also relates to the mesh obtained by this method.

13 Claims, 7 Drawing Sheets

(56) References Cited

U.S. PATENT DOCUMENTS

| | | | |
|---|---|---|---|
| 3,124,136 A | 3/1964 | Usher | |
| 3,272,204 A | 9/1966 | Charles et al. | |
| 3,276,448 A | 10/1966 | Usher | |
| 3,320,649 A | 5/1967 | Naimer | |
| 3,364,200 A | 1/1968 | Ashton et al. | |
| 3,570,482 A | 3/1971 | Emoto et al. | |
| 3,718,725 A | 2/1973 | Hamano | |
| 4,006,747 A | 2/1977 | Kronenthal et al. | |
| 4,060,081 A | 11/1977 | Yannas et al. | |
| 4,173,131 A | 11/1979 | Pendergrass et al. | |
| 4,193,137 A | 3/1980 | Heck | |
| 4,248,064 A | 2/1981 | Odham | |
| 4,294,241 A | 10/1981 | Miyata | |
| 4,307,496 A * | 12/1981 | Nakagaki | D04B 21/10 |
| | | | 28/168 |
| 4,307,717 A | 12/1981 | Hymes et al. | |
| 4,338,800 A | 7/1982 | Matsuda | |
| 4,476,697 A | 10/1984 | Schafer et al. | |
| 4,487,865 A | 12/1984 | Balazs et al. | |
| 4,500,676 A | 2/1985 | Balazs et al. | |
| 4,511,653 A | 4/1985 | Play et al. | |
| 4,527,404 A | 7/1985 | Nakagaki et al. | |
| 4,591,501 A | 5/1986 | Cioca | |
| 4,597,762 A | 7/1986 | Walter et al. | |
| 4,603,695 A | 8/1986 | Ikada et al. | |
| 4,631,932 A | 12/1986 | Sommers | |
| 4,670,014 A | 6/1987 | Huc et al. | |
| 4,709,562 A | 12/1987 | Matsuda | |
| 4,748,078 A | 5/1988 | Doi et al. | |
| 4,759,354 A | 7/1988 | Quarfoot | |
| 4,769,038 A | 9/1988 | Bendavid et al. | |
| 4,796,603 A | 1/1989 | Dahlke et al. | |
| 4,813,942 A | 3/1989 | Alvarez | |
| 4,841,962 A | 6/1989 | Berg et al. | |
| 4,854,316 A | 8/1989 | Davis | |
| 4,925,294 A | 5/1990 | Geshwind et al. | |
| 4,931,546 A | 6/1990 | Tardy et al. | |
| 4,942,875 A | 7/1990 | Hlavacek et al. | |
| 4,948,540 A | 8/1990 | Nigam | |
| 4,950,483 A | 8/1990 | Ksander et al. | |
| 4,970,298 A | 11/1990 | Silver et al. | |
| 4,976,737 A | 12/1990 | Leake | |
| 5,002,551 A | 3/1991 | Linsky et al. | |
| 5,015,584 A | 5/1991 | Brysk | |
| 5,116,357 A | 5/1992 | Eberbach | |
| 5,147,374 A | 9/1992 | Fernandez | |
| 5,162,430 A | 11/1992 | Rhee et al. | |
| 5,171,273 A | 12/1992 | Silver et al. | |
| 5,176,692 A | 1/1993 | Wilk et al. | |
| 5,192,301 A | 3/1993 | Kamiya et al. | |
| 5,195,542 A | 3/1993 | Gazielly et al. | |
| 5,196,185 A | 3/1993 | Silver et al. | |
| 5,201,745 A | 4/1993 | Tayot et al. | |
| 5,201,764 A | 4/1993 | Kelman et al. | |
| 5,206,028 A | 4/1993 | Li | |
| 5,217,493 A | 6/1993 | Raad et al. | |
| 5,254,133 A | 10/1993 | Seid | |
| 5,256,418 A | 10/1993 | Kemp et al. | |
| 5,258,000 A | 11/1993 | Gianturco | |
| 5,263,983 A | 11/1993 | Yoshizato et al. | |
| 5,304,595 A | 4/1994 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,334,527 A | 8/1994 | Brysk | |
| 5,339,657 A | 8/1994 | McMurray | |
| 5,350,583 A | 9/1994 | Yoshizato et al. | |
| 5,356,432 A | 10/1994 | Rutkow et al. | |
| 5,368,549 A | 11/1994 | McVicker | |
| 5,368,602 A | 11/1994 | de la Torre | |
| 5,370,650 A | 12/1994 | Tovey et al. | |
| 5,376,375 A | 12/1994 | Rhee et al. | |
| 5,376,376 A | 12/1994 | Li | |
| 5,397,331 A | 3/1995 | Himpens et al. | |
| 5,399,361 A | 3/1995 | Song et al. | |
| 5,413,791 A | 5/1995 | Rhee et al. | |
| 5,425,740 A | 6/1995 | Hutchinson, Jr. | |
| 5,428,022 A | 6/1995 | Palefsky et al. | |
| 5,433,996 A | 7/1995 | Kranzler et al. | |
| 5,441,491 A | 8/1995 | Verschoor et al. | |
| 5,441,508 A | 8/1995 | Gazielly et al. | |
| 5,456,693 A | 10/1995 | Conston et al. | |
| 5,456,711 A | 10/1995 | Hudson | |
| 5,466,462 A | 11/1995 | Rosenthal et al. | |
| 5,480,644 A | 1/1996 | Freed | |
| 5,487,895 A | 1/1996 | Dapper et al. | |
| 5,490,984 A | 2/1996 | Freed | |
| 5,512,291 A | 4/1996 | Li | |
| 5,512,301 A | 4/1996 | Song et al. | |
| 5,514,181 A | 5/1996 | Light et al. | |
| 5,522,840 A | 6/1996 | Krajicek | |
| 5,523,348 A | 6/1996 | Rhee et al. | |
| 5,536,656 A | 7/1996 | Kemp et al. | |
| 5,543,441 A | 8/1996 | Rhee et al. | |
| 5,565,210 A | 10/1996 | Rosenthal et al. | |
| 5,567,806 A | 10/1996 | Abdul-Malak et al. | |
| 5,569,273 A | 10/1996 | Titone et al. | |
| RE35,399 E | 12/1996 | Eisenberg | |
| 5,593,441 A | 1/1997 | Lichtenstein et al. | |
| 5,595,621 A | 1/1997 | Light | |
| 5,601,571 A | 2/1997 | Moss | |
| 5,607,474 A | 3/1997 | Athanasiou et al. | |
| 5,607,590 A | 3/1997 | Shimizu | |
| 5,614,587 A | 3/1997 | Rhee et al. | |
| 5,618,551 A | 4/1997 | Tardy et al. | |
| 5,634,931 A | 6/1997 | Kugel | |
| 5,639,796 A | 6/1997 | Lee | |
| 5,665,391 A | 9/1997 | Lea | |
| 5,667,839 A | 9/1997 | Berg | |
| 5,676,967 A | 10/1997 | Williams et al. | |
| 5,681,568 A | 10/1997 | Goldin et al. | |
| 5,686,090 A | 11/1997 | Schilder et al. | |
| 5,686,115 A | 11/1997 | Voumakis et al. | |
| 5,690,675 A | 11/1997 | Sawyer et al. | |
| 5,695,525 A | 12/1997 | Mulhauser et al. | |
| 5,697,978 A | 12/1997 | Sgro | |
| 5,700,476 A | 12/1997 | Rosenthal et al. | |
| 5,700,477 A | 12/1997 | Rosenthal et al. | |
| 5,702,416 A | 12/1997 | Kieturakis et al. | |
| 5,709,934 A | 1/1998 | Bell et al. | |
| 5,711,960 A | 1/1998 | Shikinami | |
| 5,716,409 A | 2/1998 | Debbas | |
| 5,720,981 A | 2/1998 | Eisinger | |
| 5,732,572 A | 3/1998 | Litton | |
| 5,743,917 A | 4/1998 | Saxon | |
| 5,749,895 A | 5/1998 | Sawyer et al. | |
| 5,752,974 A | 5/1998 | Rhee et al. | |
| 5,766,246 A | 6/1998 | Mulhauser et al. | |
| 5,766,631 A | 6/1998 | Arnold | |
| 5,769,864 A | 6/1998 | Kugel | |
| 5,771,716 A | 6/1998 | Schlussel | |
| 5,785,983 A | 7/1998 | Furlan | |
| 5,800,541 A | 9/1998 | Rhee et al. | |
| 5,814,328 A | 9/1998 | Gunasekaran | |
| 5,833,705 A | 11/1998 | Ken et al. | |
| 5,840,011 A | 11/1998 | Landgrebe et al. | |
| 5,861,034 A | 1/1999 | Taira et al. | |
| 5,863,984 A | 1/1999 | Doillon et al. | |
| 5,869,080 A | 2/1999 | McGregor et al. | |
| 5,871,767 A | 2/1999 | Dionne et al. | |
| 5,876,444 A | 3/1999 | Lai | |
| 5,891,558 A | 4/1999 | Bell et al. | |
| 5,899,909 A | 5/1999 | Claren | |
| 5,906,937 A | 5/1999 | Sugiyama et al. | |
| 5,910,149 A | 6/1999 | Kuzmak | |
| 5,911,731 A | 6/1999 | Pham et al. | |
| 5,916,225 A | 6/1999 | Kugel | |
| 5,919,232 A | 7/1999 | Chaffringeon et al. | |
| 5,919,233 A | 7/1999 | Knopf et al. | |
| 5,922,026 A | 7/1999 | Chin | |
| 5,931,165 A | 8/1999 | Reich et al. | |
| 5,942,278 A | 8/1999 | Hagedorn et al. | |
| 5,962,136 A | 10/1999 | Dewez et al. | |
| 5,972,022 A | 10/1999 | Huxel | |

(56) References Cited

U.S. PATENT DOCUMENTS

| | | |
|---|---|---|
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D'Aversa et al. |
| 6,113,623 A | 9/2000 | Sgro |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,289,700 B1 * | 9/2001 | Gangi .................. D02G 3/42 28/144 |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |

(56) References Cited

U.S. PATENT DOCUMENTS

| | | |
|---|---|---|
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III |
| 7,682,381 B2 | 3/2010 | Rakos et al. |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2002/0087174 A1 | 7/2002 | Cabello |
| 2002/0095218 A1 | 7/2002 | Carr et al. |
| 2003/0086975 A1 | 5/2003 | Ringeisen |
| 2003/0106346 A1 | 6/2003 | Matsumoto |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0105526 A1 | 4/2009 | Piroli Torelli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li |
| 2009/0318752 A1 | 12/2009 | Evans et al. |
| 2010/0104608 A1 | 4/2010 | Abuzaina et al. |
| 2010/0318108 A1 | 12/2010 | Datta et al. |
| 2011/0015760 A1 | 1/2011 | Kullas |
| 2011/0022083 A1* | 1/2011 | DiMatteo ........... A61B 17/0469 606/228 |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2011/0270278 A1* | 11/2011 | Overes ................. A61B 17/842 606/144 |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1* | 6/2012 | Mortarino ............. A61F 2/0063 606/151 |
| 2012/0165937 A1 | 6/2012 | Montanari et al. |
| 2012/0179175 A1 | 7/2012 | Hammell |

(56) References Cited

U.S. PATENT DOCUMENTS

| | | | |
|---|---|---|---|
| 2012/0179176 A1 | 7/2012 | Wilson et al. | |
| 2012/0197415 A1 | 8/2012 | Montanari et al. | |
| 2012/0330093 A1* | 12/2012 | Odermatt | A61F 2/0063 |
| | | | 600/30 |
| 2013/0172915 A1* | 7/2013 | Thomas | A61B 17/06166 |
| | | | 606/151 |
| 2014/0044861 A1 | 2/2014 | Boey et al. | |
| 2014/0364684 A1 | 12/2014 | Lecuivre | |

FOREIGN PATENT DOCUMENTS

| | | | | |
|---|---|---|---|---|
| DE | 19544162 C1 | 4/1997 | | |
| DE | 19718903 A1 | 12/1997 | | |
| DE | 19751733 A1 | 12/1998 | | |
| DE | 19832634 A1 | 1/2000 | | |
| DE | 10019604 A1 | 10/2001 | | |
| DE | 10120942 A1 | 10/2001 | | |
| DE | 10043396 C1 | 6/2002 | | |
| EP | 0194192 A1 | 9/1986 | | |
| EP | 0248544 A1 | 12/1987 | | |
| EP | 0263360 A2 | 4/1988 | | |
| EP | 0276890 A2 | 8/1988 | | |
| EP | 0372969 A1 | 6/1990 | | |
| EP | 0531742 A1 | 3/1993 | | |
| EP | 544485 A1 | 6/1993 | | |
| EP | 0552576 A1 | 7/1993 | | |
| EP | 0611561 A1 | 8/1994 | | |
| EP | 614650 A2 | 9/1994 | | |
| EP | 0621014 A1 | 10/1994 | | |
| EP | 0621014 A1 * | 10/1994 | | A61F 2/0063 |
| EP | 0625891 A1 | 11/1994 | | |
| EP | 0637452 A1 | 2/1995 | | |
| EP | 0664132 A1 | 7/1995 | | |
| EP | 0705878 A2 | 4/1996 | | |
| EP | 0719527 A1 | 7/1996 | | |
| EP | 0774240 A1 | 5/1997 | | |
| EP | 0797962 A2 | 10/1997 | | |
| EP | 0800791 A1 | 10/1997 | | |
| EP | 827724 A2 | 3/1998 | | |
| EP | 0836838 A1 | 4/1998 | | |
| EP | 0847727 A1 | 6/1998 | | |
| EP | 0876808 A1 | 11/1998 | | |
| EP | 0895762 A2 | 2/1999 | | |
| EP | 898944 A2 | 3/1999 | | |
| EP | 1017415 A1 | 7/2000 | | |
| EP | 1036545 A2 | 9/2000 | | |
| EP | 1052319 A1 | 11/2000 | | |
| EP | 1055757 A1 | 11/2000 | | |
| EP | 1090590 A2 | 4/2001 | | |
| EP | 1 216 717 A1 | 6/2002 | | |
| EP | 1 216 718 A1 | 6/2002 | | |
| EP | 0693523 B1 | 11/2002 | | |
| EP | 1273312 A2 | 1/2003 | | |
| EP | 1315468 A2 | 6/2003 | | |
| EP | 1382728 A1 | 1/2004 | | |
| EP | 1382728 A1 * | 1/2004 | | D04B 21/12 |
| EP | 1484070 A1 | 12/2004 | | |
| EP | 1561480 A2 | 8/2005 | | |
| EP | 1645232 A1 | 4/2006 | | |
| EP | 1674048 A1 | 6/2006 | | |
| EP | 1691606 A1 | 8/2006 | | |
| EP | 1782848 A2 | 5/2007 | | |
| EP | 2229918 A1 | 9/2010 | | |
| EP | 2327373 A1 * | 6/2011 | | A61F 2/0063 |
| EP | 2327373 A1 | 6/2011 | | |
| FR | 2244853 A1 | 4/1975 | | |
| FR | 2257262 A1 | 8/1975 | | |
| FR | 2 308 349 A1 | 11/1976 | | |
| FR | 2453231 A1 | 10/1980 | | |
| FR | 2612392 A1 | 9/1988 | | |
| FR | 2715309 A1 | 7/1995 | | |
| FR | 2715405 A1 | 7/1995 | | |
| FR | 2 724 563 A1 | 3/1996 | | |
| FR | 2730406 A1 | 8/1996 | | |
| FR | 2744906 A1 | 8/1997 | | |
| FR | 2766698 A1 | 2/1999 | | |
| FR | 2771622 A1 | 6/1999 | | |
| FR | 2773057 A1 | 7/1999 | | |
| FR | 2774277 A1 | 8/1999 | | |
| FR | 2779937 A1 | 12/1999 | | |
| FR | 2859624 A1 | 3/2005 | | |
| FR | 2863277 A1 | 6/2005 | | |
| FR | 2876020 A1 | 4/2006 | | |
| FR | 2884706 A1 | 10/2006 | | |
| FR | 2929834 A1 | 10/2009 | | |
| FR | 2953709 A1 | 6/2011 | | |
| GB | 1174814 A | 12/1969 | | |
| GB | 2 051 153 A | 1/1981 | | |
| GB | 2306110 A | 4/1997 | | |
| JP | H0332677 A | 2/1991 | | |
| JP | H05237128 A | 9/1993 | | |
| JP | H09137380 A | 5/1997 | | |
| JP | H11146888 A | 6/1999 | | |
| JP | 2008538300 A | 10/2008 | | |
| JP | 2011078767 A | 4/2011 | | |
| WO | 89/02445 A1 | 3/1989 | | |
| WO | 89/08467 A1 | 9/1989 | | |
| WO | 90/12551 A1 | 11/1990 | | |
| WO | 92/06639 A2 | 4/1992 | | |
| WO | 92/20349 A1 | 11/1992 | | |
| WO | 93/11805 A1 | 6/1993 | | |
| WO | 9310731 A1 | 6/1993 | | |
| WO | 93/18174 A1 | 9/1993 | | |
| WO | 94/17747 A1 | 8/1994 | | |
| WO | 95/07666 A1 | 3/1995 | | |
| WO | 95/18638 A1 | 7/1995 | | |
| WO | 95/32687 A1 | 12/1995 | | |
| WO | 96/03091 A1 | 2/1996 | | |
| WO | 96/08277 A1 | 3/1996 | | |
| WO | 96/09795 A1 | 4/1996 | | |
| WO | 96/14805 A1 | 5/1996 | | |
| WO | 96/41588 A1 | 12/1996 | | |
| WO | 97/35533 A1 | 10/1997 | | |
| WO | 98/35632 A1 | 8/1998 | | |
| WO | 98/49967 A1 | 11/1998 | | |
| WO | 99/05990 A1 | 2/1999 | | |
| WO | 99/06079 A1 | 2/1999 | | |
| WO | 99/06080 A1 | 2/1999 | | |
| WO | 99/51163 A1 | 10/1999 | | |
| WO | 00/16821 A1 | 3/2000 | | |
| WO | 00/67663 A1 | 11/2000 | | |
| WO | 01/15625 A1 | 3/2001 | | |
| WO | 01/80773 A1 | 11/2001 | | |
| WO | 01/81667 A1 | 11/2001 | | |
| WO | 02/007648 A1 | 1/2002 | | |
| WO | 0217853 A2 | 3/2002 | | |
| WO | 02/078568 A1 | 10/2002 | | |
| WO | 03/002168 A1 | 1/2003 | | |
| WO | 2004004600 A1 | 1/2004 | | |
| WO | 2004071349 A2 | 8/2004 | | |
| WO | 2004078120 A2 | 9/2004 | | |
| WO | 2004103212 A1 | 12/2004 | | |
| WO | 200511280 A1 | 2/2005 | | |
| WO | 2005013863 A2 | 2/2005 | | |
| WO | 2005018698 A1 | 3/2005 | | |
| WO | 2005048708 A1 | 6/2005 | | |
| WO | 2005105172 A1 | 11/2005 | | |
| WO | 2006018552 A1 | 2/2006 | | |
| WO | 2006023444 A2 | 3/2006 | | |
| WO | 2006032812 A2 | 3/2006 | | |
| WO | 2007048099 A2 | 4/2007 | | |
| WO | 2009031035 A2 | 3/2009 | | |
| WO | 2009071998 A2 | 6/2009 | | |
| WO | WO2009/071998 | 6/2009 | | |
| WO | 2010043978 A2 | 4/2010 | | |
| WO | 2011007062 A1 | 1/2011 | | |
| WO | 2011026987 A1 | 3/2011 | | |
| WO | 2011038740 A1 | 4/2011 | | |
| WO | WO2013/098347 A1 | 7/2013 | | |

OTHER PUBLICATIONS

Machine Translation EP 0 621 014 (Year: 1994).*

(56) References Cited

OTHER PUBLICATIONS

European Search Report for EP16306383.7 date of completion is May 9, 2017 (4 pages).
Malette, W. G. et al., "Chitosan, A New Hemostatic," Ann Th. Surg., Jul. 1983, pp. 55-58, 36.
Langenbech, M. R. et al., "Comparison of biomaterials in the early postoperative period," Surg Endosc., May 2003, pp. 1105-1109, 17 (7).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Klinge, U. et al., "Foreign Body Reaction to Meshes Used for the Repair of Abdominal Wall Hernias," Eur J. Surg, Sep. 1999, pp. 665-673, 165.
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.
Junge, K. et al., "Functional and Morphologic Properties of a Modified Mesh for Inguinal Hernia Repair," World J. Surg., Sep. 2002, pp. 1472-1480, 26.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Welty, G. et al., "Functional impairment and complaints following incisional hernia repair with different polypropylene meshes," Hernia, Aug. 2001; pp. 142-147, 5.
Varum, K. et al., "In vitro degradation rates of partially N-acetylated chitosans in human serum," Carbohydrate Research, Mar. 1997, pp. 99-101, 299.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).
Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyagintseva, T. et al., "Inhibition of complement activation by water-soluble polysaccharides of some far-eastern grown seaweeds," Comparative Biochem and Physiol, Jul. 2000, pp. 209-215,126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
D'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 413-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol. 25.
Dr. S. Raz, "The Karl Mayer Guide to Tehnical Textiles," Jan. 2000, pp. 1-36, Obertshausen, Germany.
Chen, G. et al., "A Hybrid Network of Synthetic Polymer Mesh and Collagen Sponge," The Royal Society of Chemistry 2000, Chem. Commun., Jul. 2000, pp. 1505-1506.

* cited by examiner

METHOD FOR FORMING A MESH HAVING A BARBED SUTURE ATTACHED THERETO AND THE MESH THUS OBTAINED

CROSS-REFERENCE TO RELATED APPLICATIONS

This application claims benefit of and priority to European Patent Application No. 16306383.7 filed Oct. 21, 2016, the disclosure of the above-identified application is hereby incorporated by reference in its entirety.

BACKGROUND OF THE INVENTION

The present invention relates to a method for forming a prosthetic mesh having one or more barbed suture(s) attached thereto, such a prosthetic mesh being useful in the surgical field. The method of the invention allows producing a prosthetic mesh having one or more barbed suture(s) attached thereto in a reduced time and in a very cost-effective way.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias or incisional hernias (a hernia occurring through a parietal surgical scar) show themselves in the form of a bulge at the surface of the skin and are classed, for example, as umbilical or inguinal hernias or incisional hernias, depending on where they are located.

In order to repair a hernia defect, surgeons often fit a prosthesis in place which is made of synthetic mesh and replaces or strengthens the weakened anatomical tissues.

Within the meaning of the present application, a "mesh" is understood as an arrangement of biocompatible yarns, such as a textile or fabric, preferably open-worked, that is to say provided with pores that favour recolonization of tissue such as cellular growth. Such a mesh can be bioresorbable, permanent or partially bioresorbable. It is sufficiently flexible to be folded up at the time of introduction into the abdominal cavity.

Meshes for forming hernia prosthesis are well known to a person skilled in the art. The mesh can be supplied in any shape whatsoever, for example rectangular, square, circular, oval, etc., and can then be cut to suit the shape of the hernia defect. For example, the overall shape of the mesh can be circular or oval. Alternatively, the mesh can have a generally square shape or a rectangular shape.

Meshes for forming hernia prosthesis are advantageously provided as a knitted structure obtained with biocompatible yarns. Knitting methods allow obtaining knitted structure having openworked faces that promote cell recolonization after implantation.

Once implanted, the mesh must be fixed to the surroundings biological tissues, such as for example the abdominal wall. Many fixing means are available for fixing the mesh to the abdominal wall, such as tacks, staples, adhesives or sutures.

The use of sutures usually imply forming surgical knots in order to anchor the suture.

Surgical knots have been used for ages in order to anchor and allow a conventional suture, in other words a smooth suture without barbs, to perform its role in mesh fixation for example. Anyway, surgical knots reduce the tensile strength of conventional sutures by thinning and stretching the material forming the suture. Indeed, it is known that the weakest portion of any suture line is the knot.

Moreover, the tying of surgical knots introduces the potential of human error. A knot-secured conventional suture may create an uneven distribution of tension across the wound, with the higher tension burden placed at the knots. In addition, in minimally invasive laparoscopic surgery, the ability to quickly and properly tie surgical knots presents a challenge. The skill necessary for performing intra- or extracorporeal knot tying for laparoscopic surgery may be acquired only with practice and patience, yet surgeons need to master such a skill in order to properly perform closure procedures. Laparoscopic knot tying is also more mentally and physically stressful on surgeons.

Given the excessive relative wound tension on the knot and the reasonable concerns of surgeons for suture failure due to knot slippage, there is a natural tendency toward overcoming these potential issues by over-tightening knots. However, tighter knots may be worse for wound healing and strength than looser knots. Surgical knots, when tied too tightly, can cause localized hypoxia, reduced fibroblast proliferation, and excessive tissue overlap, leading to reduced strength in the healed wound.

Eventually, a surgical knot yields the highest density of foreign body material in any given suture line and the volume of a knot may be directly related to the total amount of surrounding inflammatory reaction. If minimizing the inflammatory reaction in a wound is important for optimized wound healing, then minimizing knots sizes or even eliminating knots altogether would be beneficial as long as the wound-holding strength of the suture line is not compromised.

For all these reasons, the use of barbed suture, suture with barbs, has tremendously increased in the past years. In particular, one of the most costly parts of a surgical procedure is time in the operating room.

Barbed sutures are known. They basically consist in strands of smooth suture provided with barbs on their surfaces. Barbed sutures are generally made of the same materials as conventional sutures and offer several advantages for fixing meshes to the abdominal wall compared with conventional sutures. A barbed suture includes an elongated body that has one or more spaced barbs, that project from the surface of the suture body along the body length.

The barbs are generally arranged to allow passage of the barbed suture in one direction through tissue but resist movement of the barbed suture in the opposite direction (one-way suture). One advantage of barbed sutures is the provision of a non-slip property.

Barbed sutures are known for use in laparoscopic and endoscopic procedures. The number of barbs needed for a particular suture may be influenced by the size of the wound and the strength required to fix the mesh. Like a conventional suture, a barbed suture may be inserted into tissue using a surgical needle.

In some circumstances, a random configuration of barbs on the exterior surface of the suture is preferred to achieve optimal fixing of the mesh. However, in other circumstances, where the tissue repair needed is relatively small, a reduced number of barbs may be desired.

Various methods of forming barbs on sutures have been proposed such as mechanical cutting, laser cutting, injection molding, stamping, extrusion and the like. However, such methods may be difficult or costly, in particular when a specific arrangement or configuration of barbs is needed for an appropriate surgical procedure.

For example, conventional cutting methods of forming barbs may involve cutting with a blade into the elongate body of the suture, where the elongate body may be a monofilament for example. Barbed sutures may be fabricated from monofilament fibers by a micro-machining technique, which escarpes barbs into the fiber around the circumference in a variety of configurations. Cutting meth s have therefore significant drawbacks as they weaken the core of the suture and narrow its functional diameter. Moreover, they are costly and have slow manufacturing cycle time.

Accordingly, there is a continuous need for methods of forming barbs on a suture that are less difficult to implement, more efficient and cost effective. There is also a continuous need for methods allowing varying the size, the location and the depth of the barbs, as well as the amount of barbs present on the suture, depending on the contemplated surgical application.

In particular, there is a need for providing a mesh having one or more barbed suture(s) attached thereto, so that the surgeon does not have to waste time looking for a suture at the time he needs to fix the mesh to the biological tissue during the implantation.

A first aspect of the invention is a method for forming a prosthetic mesh having at least a barbed suture attached thereto, said barbed suture comprising an elongate body provided with barbs extending substantially radially out from said elongate body, said method comprising the following steps:

a) producing a knitted structure on a warp knitting machine comprising at least one needle-bed comprising at least three guide bars, a first guide bar B1, a second guide bar B2 and a third guide bar B3, said first guide bar B1 being threaded with first yarns of a biocompatible material, said second guide bar B2 being threaded with second yarns of a biocompatible material, said third guide bar B3 being threaded with third yarns of a biocompatible material, said knitted structure being produced on a determined length along the warp direction corresponding to a total number of N stitches ranging from 1 to N completed along said warp direction by the machine, N being an integer above 7, wherein
  i) a first knit portion is produced along stitches ranging from 1 to x, where $1<x<N$, in which the knitting patterns followed by the first, the second and the third guide bars (B1, B2, B3) produce an openworked knit capable of favoring cellular growth,
  ii) a second knit portion is produced for stitches ranging from (x+1) to N, in which the knitting pattern followed by said second and third guide bars (B2, B3) produces chain stitches and the knitting pattern followed by the first guide bar B1 produces at least a partial weft in which said first yarns complete weft stitches with at least one of said chain stitches, thereby producing at least one weft stitched chain stitch, b) cutting the second knit portion along the warp direction on both sides of said at least one weft stitched chain stitch and along an edge separating the second knit portion from the first knit portion, so as to remove the second knit portion from the knitted structure while maintaining said weft stitched chain stitch attached to the first knit portion, wherein the first knit portion forms the mesh and the second or third yarn forming part of said at least one weft stitched chain stitch forms said elongate body of said barbed suture attached thereto, the first yarns cuts extending from said weft stitches of said at least one weft stitched chain stitch forming said barbs of said barbed suture.

In the prosthetic mesh obtained by the method of the invention, the barbed suture therefore comprises an elongate body made of a yarn of a biocompatible material coming either from guide bar B2 (second yarn) or from guide bar B3 (third yarn), provided with barbs extending substantially radially out from said elongate body, said barbs being first yarns cuts made of a biocompatible material, where said first yarns cuts are stitched to said second or third yarn forming said elongate body. The first yarn cuts result from the cutting of the second knit portion on both sides of the at least one weft stitched chain stitch. In embodiments, said elongate body(ies) of said barbed suture(s) is/are formed of second yarns only.

In the present application, "N" and "x" correspond to numbers of stitches and are therefore integers.

In the present application, by "knit capable of favoring cellular growth" is meant a knit the knitting pattern of which allows creating voids, pores, channels on the surfaces and/or within the thickness of the knit so that cells may colonize the knit once the knit is implanted in the body of a human being.

Another aspect of the invention is a prosthetic mesh having at least a barbed suture attached thereto, said barbed suture comprising an elongate body made of a yarn of biocompatible material, provided with barbs extending substantially radially out from said elongate body, said barbs being yarns cuts made of a biocompatible material, where said yarns cuts are stitched to said yarn forming said elongate body, said prosthetic mesh being obtained by the method above.

In a first step, step a), of the method of the invention, a knitted structure is produced on a warp knitting machine. The warp knitting machine comprises at least one needle-bed comprising at least three guide bars, a first guide bar B1, a second guide bar B2 and a third guide bar B3. The first guide bar B1 is threaded with first yarns of a biocompatible material, the second guide bar B2 is threaded with second yarns of a biocompatible material, the third guide bar B3 being threaded with third yarns of a biocompatible material. The knitted structure is produced on a determined length along the warp direction corresponding to a total number of N stitches ranging from 1 to N completed along said warp direction by the machine, N being an integer above 7. During this step a), i) a first knit portion is produced along stitches ranging from 1 to x, where $1<x<N$, in which the knitting patterns followed by the first, the second and the third guide bars (B1, B2, B3) produce an openworked knit capable of favoring cellular growth, and ii) a second knit portion is produced for stitches ranging from (x+1) to N, in which the knitting pattern followed by said second and third guide bars (B2, B3) produces chain stitches and the knitting pattern followed by the first guide bar B1 produces at least a partial weft in which said first yarns complete weft stitches with at least one of said chain stitches, thereby producing at least one weft stitched chain stitch.

The warp knitting machine may be for example a crochet machine or a raschel knitting machine or a Jacquard machine. Warp knitting machines have a warp yarn for each needle.

By "chain stitch" is meant according to the present application a stitch construction where both over and underlapping are always carried out across the same needle. One chain stitch of a knit therefore involves only one warp yarn, in other words involves only one yarn in the warp direction. The tensile strength of one chain stitch is therefore the tensile strength of said single warp yarn involved in the construction of the chain stitch.

The warp knitting machine may comprise one or more needle-bed(s). For example, the warp knitting machine may comprise two needle-beds. Such double needle-bed machines allow producing bidimensional knits and three-dimensional knits.

In the present application by "bidimensional knit" is meant a knit obtained on a warp knitting machine with the use of one needle-bed only, whatever the number of needle-beds present in the machine, and whatever the number of guide bars present in said one needle-bed. For example, a bidimensional knit may be obtained with two guide bars or more, as long as said guide bars all belong to one needle-bed only. Bidimensional knits may also be obtained on a Jacquard machine, where each guide bar elements are independent.

In the present application by "three-dimensional knit" is meant a knit obtained on a warp knitting machine with the use of two needle-beds, with yarns crossing from a needle-bed to the other.

In embodiments, the warp knitting machine comprises two needle-beds, a first needle-bed comprising said first, second and third guide bars (B1, B2, B3) described above, and a second needle-bed comprising fourth guide bar B4, fifth guide bar B5 and sixth guide bar B6. The fourth guide bar B4 is threaded with fourth yarns of a biocompatible material, the fifth guide bar B5 is threaded with fifth yarns of a biocompatible material, the sixth guide bar B6 is threaded with sixth yarns of a biocompatible material. In such embodiments, the first and second knit portions may be produced by using the six guide bars (B1, B2, B3, B4, B5 and B6).

In such embodiments, step a) may comprise a step 0) occurring before step a)i) as follows:

0) a connecting knit portion is produced along stitches ranging from 1 to y, where $1<y<x<N$, in which the knitting patterns followed by first, second, third, fourth, fifth and sixth guide bars (B1, B2, B3, B4, B5, B6) produce a three-dimensional openworked knit capable of favoring cellular growth, said knit having a first face produced on said first needle-bed by said first, second and third yarns from said first, second and third guide bars (B1, B2, B3), and a second face, produced on said second needle-bed by said fourth, fifth and sixth yarns from said fourth, fifth and sixth guide bars (B4, B5, B6), said first and second faces being linked together by some of the second, third, fourth and/or fifth yarns, preferably by some of the third and/or fourth yarns, crossing from the first needle-bed to the second needle-bed and vice-versa, thereby forming linking yarns, and, in step i), the first knit portion is produced along stitches ranging from (y+1) to x, in which the knitting patterns followed by the first, second and third guide bars (B1, B2, B3) produce on the first needle-bed a first bidimensional openworked knit capable of favoring cellular growth, and in which the knitting patterns followed by the fourth, fifth and sixth guide bars (B4, B5, B6) produce on the second needle-bed a second bidimensional openworked knit capable of favoring cellular growth, said first and second bidimensional openworked knits being independent from each other, and, in step ii), the second knit portion is produced for stitches ranging from (x+1) to N, in which:

on said first needle-bed, a first needle-bed second knit portion is produced, in which the knitting pattern followed by said second and third guide bars (B2, B3) produces chain stitches and the knitting pattern followed by the first guide bar B1 produces at least a partial weft in which said first yarns complete weft stitches with at least one of said chain stitches, thereby producing at least one first weft stitched chain stitch, on said second needle-bed, a second needle-bed second knit portion is produced, in which the knitting pattern followed by said fourth and fifth guide bars (B4, B5) produces chain stitches and the knitting pattern followed by the sixth guide bar B6 produces at least a partial weft in which said sixth yarns complete weft stitches with at least one of said chain stitches, thereby producing at least one second weft stitched chain stitch, said first needle-bed second knit portion and said second needle-bed second knit portion being independent from each other.

In the present application, "y" corresponds to a number of stitches and is therefore an integer.

In the present application, by "independent knits" with respect to two knits produced, for example simultaneously, on a double-bed knitting machine, is meant one knit produced on the first needle-bed and a second knit produced on the second needle-bed, with no yarns from one needle-bed crossing to the other needle-bed during the production of said two independent knits.

In the present application, the terms "weft stitched chain stitch", "first weft stitched chain stitch" and "second weft stitched chain stitch" all relate to weft stitched chain stitches obtained according to the method of the invention and generally referred to as "weft stitched chain stitch", the terms "first weft stitched chain stitch" and "second weft stitched chain stitch" being used for sake of clarity when two needle-beds are used, as it may be useful to distinguish the first weft stitched chain stitches obtained with the first needle-bed from the second weft stitched chain stitches obtained with the second needle-bed.

In embodiments where the warp knitting machine comprises a first needle-bed comprising first, second and third guide bars (B1, B2, B3) and a second needle-bed comprising fourth, fifth and sixth guide bars (B4, B5, B6) as described above, the cutting step b°) may comprise the following steps:

cutting the first needle-bed second knit portion along the warp direction on both sides of said at least one first weft stitched chain stitch and along an edge separating the first needle-bed second knit portion from the first bidimensional openworked knit, so as to remove the first needle-bed second knit portion from the knitted structure while maintaining said first weft stitched chain stitch attached to the first bidimensional openworked knit, cutting the second needle-bed second knit portion along the warp direction on both sides of said at least one second weft stitched chain stitch and along an edge separating the second needle-bed second knit portion from the second bidimensional openworked knit, so as to remove the second needle-bed second knit portion from the knitted structure while maintaining said second weft stitched chain stitch attached to the second bidimensional openworked knit, and the method may further comprise the following steps occurring after step b°):

c°) optionally cutting said linking yarns from the three-dimensional openworked knit obtained in step a)0) along stitches ranging from 2 to y, d°) opening the knitted structure so as to spread in a single plane the part of the knitted structure obtained from the first needle-bed and the part of the knitted structure obtained from the second needle-bed, wherein the first bidimensional openworked knit, the connecting knit portion, optionally cut according to step c°), and the second bidimensional openworked knit form altogether the mesh; the second or third yarn forming part of said at least one first weft stitched chain stitch forms the elongate body of a first barbed suture attached to the first bidimensional openworked knit, the first yarns cuts extending from said weft stitches of said at least one first weft stitched chain stitch forming said barbs of said first barbed suture; the fourth or fifth yarn forming part of said at least one second weft stitched chain stitch forms the elongate body of a second barbed suture attached to the second bidimensional openworked knit, the sixth yarns cuts extending from said weft stitches of said at least one second weft stitched chain stitch forming said barbs of said second barbed suture.

In the present application, the terms "barbed suture", "first barbed suture" and "second barbed suture" all relate to barbed sutures obtained according to the method of the invention and generally referred to as "barbed suture", the terms "first barbed suture" and "second barbed suture" being used for sake of clarity when two needle-beds are used, as it may be useful to distinguish the first barbed sutures obtained with the first needle-bed from the second barbed sutures obtained with the second needle-bed.

As will appear from the description below, the method of the invention allows producing prosthetic meshes having barbed sutures attached thereto in a very simple, easy and rapid process. In particular the method of the invention is a cost effective process as there is no need to use sophisticated cutting machines with blades for performing cuts into the body of a monofilament.

It is known that warp knitting machines are capable of producing knits at high production rates. In addition, the knits produced may also show a very long dimension along the warp direction, which is the direction of manufacturing the knit.

As an example, with current existing warp knitting machines, knits of at least 300 meters long may be produced. For example, if the knitted structure of step a) of the method of the invention has a length L corresponding to the N stitches, a plurality of such knitted structures of length L may be obtained on a length of 300 meters, by simply repeating the knitting patterns of stitches 1 to N as many times as possible on the length of 300 meters. The method of the invention therefore allows manufacturing a plurality of meshes having barbed sutures attached thereto on 300 meters long in a very cost effective way, and in particular in only one knitting step.

The three-dimensional openworked knit obtained during step a)0) of the method of the invention is capable of favoring cellular growth and may be obtained thanks to all knitting patterns known from the art allowing to produce a knit with pores, voids, etc. on a double needle-bed warp machine by using the two needle-beds of the machine. Such knitting patterns are well known.

Examples of knitting three-dimensional knits suitable for the present invention are given in the documents WO99/05990, WO2009/031035 and WO2009/071998.

The bidimensional openworked knits obtained during step a)i) of the method of the invention are capable of favoring cellular growth and may be obtained thanks to all knitting patterns known from the art allowing to produce a knit with pores, voids, etc. using only one needle bed of a warp knitting machine. Such knitting patterns are well known.

Examples of knitting two-dimensional knits suitable for the present invention are given in the document WO2009/071998.

In addition, the barbs created in the barbed suture(s) of the mesh produced according to the method for the invention are ineradicable since they are made of yarns cuts, namely first yarns cuts and/or sixth yarns cuts, that stitch through chain stitches pillar.

In embodiments, the knitting pattern followed by the first guide bar B1 during step a)ii) produces at least a partial weft in which said first yarns complete weft stitches with a plurality of chain stitches, thereby producing a plurality of weft stitched chain stitches, and wherein the cutting of step b) is repeated for each weft stitched chain stitch, thereby producing a plurality of barbed sutures attached to the first knit portion.

In embodiments where the warp knitting machine comprises two needle-beds with three guide bars each as described above, the knitting pattern followed by the first guide bar B1 on the first needle-bed, respectively by the sixth guide bar B6 on the second needle-bed, during step a)ii), may produce at least a partial weft in which said first yarns, respectively said sixth yarns, complete weft stitches with a plurality of chain stitches, thereby producing a plurality of first and second weft stitched chain stitches. In such embodiments, the cutting of step b) may be repeated for each of said first and second weft stitched chain stitches, thereby producing a plurality of first barbed sutures attached to the first bidimensional openworked knit, respectively a plurality of second barbed sutures attached to the second bidimensional openworked knit.

The method of the invention therefore allows manufacturing a mesh having a plurality of barbed sutures of significant length each, the plurality of barbed sutures being attached to the mesh.

In current existing warp knitting machines, a high number of chain stitches may be produced along the width of a knit. As an example, 286 or more chain stitches may be produced on the width of a knit. The method of the invention therefore allows producing a mesh having for example from 2 to 20 barbed sutures attached thereto in one single knitting step Guide bar B1, respectively guide bar B6, may be fed continuously or intermittently with the first yarns, respectively the sixth yarns, during step a)ii). In embodiments, guide bar B1, respectively guide bar B6, is fed continuously with the first yarns, respectively the sixth yarns, during step a)ii).

The method of the invention further allows producing meshes having barbed suture(s) having different functional portions along their length. In particular, the method of the invention allows producing meshes having barbed suture(s) having active portions, namely portions provided with barbs, and passive portions, namely portions free of any barbs. The passive portions may be obtained by simply stopping the feeding of the first guide bar B1, respectively the sixth guide bar B6, with the first yarns, respectively the sixth yarns, for a certain period of time during the knitting process of step a°)ii) of the method of the invention. Meshes with barbed sutures having alternating active portions and passive portions may therefore be obtained by simply intermittently feeding the first guide bar B1, respectively the sixth guide bar B6, during the knitting process. In embodiments, the first guide bar B1, alternatively the sixth guide bar B6, is fed intermittently with said first yarns, alternatively sixth yarns.

Alternatively, barbed sutures having alternating active portions and passive portions may be obtained by modifying the knitting pattern of guide bar B1, respectively of guide bar B6, so that, for one or several determined time periods during step a)ii) of production of the knitted structure, the first yarns, respectively the sixth yarns, do not complete any weft stitches with said weft stitched chain stitch(es).

The method of the invention further allows varying and selecting the length of the barbs according to an easy process. Indeed, the length of the barbs of the barbed sutures of the meshes obtained with the method of the invention will be dependent first on the distance left between a weft stitched chain stitch and the two adjacent chain stitches on both sides of said weft stitched chain stitch, said distance being a function of the knitting pattern used during step a)ii), and second on the location of the cutting line on said distance at the time of the cutting step b) of the method of the invention. The distance left between a weft stitched chain stitch and the two adjacent chain stitches in the first needle-bed second knit portion will be function of the threading-in of the three guide bars (B1, B2, B3) on the first needle-bed, in particular of the threading-in of the second and third guide bars B2 and B3, and optionally of the first guide bar B1. In the same manner, the distance left between a weft stitched chain stitch and the two adjacent chain stitches in the second needle-bed second knit portion will be function of the threading-in of the three guide bars (B4, B5, B6) on the second needle-bed, in particular of the threading-in of the fourth and fifth guide bars (B4, B5) forming the chain stitches. The greater the distance desired, the more empty needles left between two full needles. On the contrary, the smaller the distance desired between two adjacent weft stitched chain stitches, the less empty needles left between two full needles.

In embodiments where the warp knitting machine comprises only one needle-bed, the knitting pattern followed by the first guide bar B1, the second guide bar B2 and the third guide bar B3 may be as described below for a number N of stitches equal to 70, with x=30. All the knitting patterns are given according to the ISO 11676 standard (publication year 2014):

1°) during step a)i), production of the first knit portion capable of favoring cellular growth according to the following knitting pattern for stitches ranging from 1 to 30:
Bar B1: (5.4/3.2/0.1)×10//
Bar B2: (5.4/3.2/0.1)×10//
Bar B3: (0.1/2.3/5.4)×10//

2°) during step a)ii), production of the second knit portion according to the following knitting pattern for stitches ranging from 31 to 70:
Bar B1: (0.0/2.3/5.5/3.2)×10//
Bar B2: (2.3/2.3/3.2/3.2)×10//
Bar B3: (2.3/2.3/3.2/3.2)×10// wherein, in both steps, B1 is threaded 1 full, 3 empty, B2 is threaded 1 full, 3 empty and B3 is threaded 1 full, 3 empty, along the whole width of the machine.

Such a pattern results in a distance between a weft stitched chain stitch and the two adjacent chain stitches of about 3.5 mm.

In embodiments, where the warp knitting machine comprises a first needle-bed comprising three guide bars B1, B2 and B3 and a second needle-bed comprising three guide bars B4, B5 and B6, the knitting patterns followed by the six guide bars may be as described below for a number N of stitches equal to 70, with x=30, and y=6. All the knitting patterns are given according to the ISO 11676 standard (publication year 2014):

1°) During step a)0): for stitches ranging from 1 to 6, production of a three-dimensional openworked knit capable of favoring cellular growth (connecting knit portion) according to the following knitting pattern:
B1: (5.4.3.3/3.2.1.1/0.1.3.3)×2//
B2: (5.4.3.3/3.2.1.1/0.1.3.3)×2//
B3: 0.1.0.1/2.3.2.3/5.4.2.2/0.1.2.2/2.3.4.4/5.4.2.2//
B4: 0.1.0.1/2.3.2.3/4.4.5.4/2.2.0.1/2.2.2.3/4.4.5.4//
B5: (3.3.5.4/3.3.3.2/1.1.0.1)×2//
B6: (3.3.5.4/3.3.3.2/1.1.0.1)×2//

2°) During step a)i): for stitches ranging from 7 to 30: production of the first knit portion as follows:

On the first needle-bed, production of a first bidimensional openworked knit capable of favoring cellular growth according to the following knitting pattern:
B1: (5.4.3.3/3.2.1.1/0.1.3.3)×8//
B2: (5.4.3.3/3.2.1.1/0.1.3.3)×8//
B3: (0.1.2.2/2.3.4.4/5.4.2.2)×8//

On the second needle-bed, production of a second bidimensional openworked knit capable of favoring cellular growth according to the following knitting pattern:
B4: (2.2.0.1/2.2.2.3/4.4.5.4)×8//
B5: (3.3.5.4/3.3.3.2/1.1.0.1)×8//
B6: (3.3.5.4/3.3.3.2/1.1.0.1)×8//

3°) During step a)ii): for stitches ranging from 31 à 70: production of the second knit portion as follows:

On the first needle-bed, production of first needle-bed second knit portion according to the following knitting pattern:
B1: (0.0.0.0/2.3.4.4/5.5.5.5/3.2.1.1)×10//
B2: (2.3.2.2/2.3.3.3/3.2.3.3/3.2.2.2)×10//
B3: (2.3.2.2/2.3.3.3/3.2.3.3/3.2.2.2)×10//

On the second needle-bed, production of second needle-bed second knit portion according to the following knitting pattern:
B4: (2.2.2.3/2.2.2.3/3.3.3.2/3.3.3.2)×10//
B5: (2.2.2.3/2.2.2.3/3.3.3.2/3.3.3.2)×10//
B6: (1.1.0.0/0.0.2.3/4.4.5.5/5.5.3.2)×10//

For example, in all the steps, all the guide bars (B1, B2, B3, B4, B5, B6) may be threaded 1 full, 3 empty along the whole width of the machine.

The method of the invention also allows varying and selecting the amount or number of barbs along the length of the suture in an easy way. In particular, the method of the invention allows selecting a specific frequency of barbs along the length of the suture, in other words a number of barbs per centimeter of suture. Such a frequency will depend on the knitting pattern followed by the first guide bar B1, respectively the sixth guide bar B6, threaded with the first yarns, respectively the sixth yarns. In particular, the more weft stitches completed along the warp direction of the chain stitch, the more weft stitches present on the weft stitched chain stitch in the end, and the higher the frequency of barbs on the resulting barbed suture. In embodiments, the knitting pattern followed by the first guide bar B1, respectively the sixth guide bar B6, produces a partial weft in which said first yarns, respectively said sixth yarns, complete from about 4 to about 15 weft stitches/cm along a length of each said weft stitched chain stitch.

In addition, the method of the invention allows producing meshes having barbed suture(s) attached thereto without affecting the tensile strength of the elongate body of the barbed suture(s). Indeed, contrary to cutting methods of the prior art which create the barbs by performing cuttings in the elongate body of the suture, made of a monofilament for example, the method of the invention leaves the yarn forming the elongate body of the suture integrate. The integrity of the yarn is not affected. As a consequence, the tensile strength of the yarn forming the elongate body of a barbed suture of the mesh obtained by the method of the invention is not affected by the presence of the barbs. Moreover, the method of the invention allows using both monofilaments and multifilaments yarns as the elongate body of the suture, whereas the methods of the prior art involving cutting steps request that the elongate body be a unitary structure, such as a monofilament yarn.

In embodiments, the chain stitch yarns, that will form the elongate body of the barbed suture(s), in particular the second, third, fourth and/or fifth yarns, may be monofilaments or multifilaments. In embodiments, the chain stitch yarns are monofilaments yarns, for example having a diameter ranging from about 0.07 mm to about 0.30 mm. In embodiments, the chain stitch yarns are multifilaments. Existing multifilament yarns may show high tenacity, in other words, high tensile strength. In embodiments, the chain stitch yarns may be multifilament yarns having a tensile strength ranging from about 25 cN/dTex to about 40 cN/dTex, for example a tensile strength of about 35 cN/dTex.

In embodiments, the chain stitch yarns may be multifilament yarns having a thickness ranging from 30 to 500 dTex, for example a thickness of 165 dTex.

In embodiments, the first yarns, that will form the barbs of the barbed suture, in particular of the first barbed suture when two needle-beds are used, may be monofilaments or multifilaments. In embodiments, the first yarns are monofilaments. In embodiments, the sixth yarns, that will form the barbs of the second barbed suture, may be monofilaments or multifilaments. In embodiments, the sixth yarns are monofilaments. Monofilaments allow obtaining barbs with higher mechanical properties. For example, the first yarns and the sixth yarns may be selected from monofilaments having a diameter ranging from about 0.15 mm to about 0.30 mm, for example from about 0.20 mm to about 0.30 mm.

The method of the invention allows producing meshes with barbed suture(s), with barbs having varying surface area in a very easy way. In particular, the size and/or the surface area of the barbs of a barbed suture of the mesh obtained by the method of the invention will be dependent on the size of the diameter of the first yarns, respectively the sixth yarns. In embodiments, the first yarns and/or the sixth yarns are monofilaments showing a diameter ranging from 0.07 mm to 0.30 mm. Such a diameter allows obtaining a good fixation of the barbed suture within the biological tissues.

Barbs of varying size may be desired depending on the contemplated surgical application of the mesh. For joining fat and relatively soft tissues, larger barbs may be desired, whereas smaller barbs may be more suitable for collagen-dense tissues. With the method of the invention, the production of small or alternatively large barbs may be easily obtained by simply selecting monofilament yarns for the first and/or sixth yarns of adequate diameters. For example, for obtaining a barbed suture with large barbs according to the method of the invention, monofilament yarns with a diameter ranging from 0.20 mm to 0.30 mm may be used for the first and/or sixth yarns. In embodiments, the first and/or sixth yarns are monofilament yarns showing a diameter ranging from 0.20 mm to 0.30 mm. Alternatively, for obtaining a barbed suture with small barbs according to the method of the invention, monofilament yarns with a diameter ranging from 0.07 mm to 0.10 mm may be used for the first and/or sixth yarns. In embodiments, the first and/or sixth yarns are monofilament yarns having a diameter ranging from 0.07 mm to 0.10 mm.

In some embodiments, a combination of large and small barbs within the same suture may be desirable, for example when the mesh of the invention is used in tissue repair with differing layer structures. Use of the combination of large and small barbs with the same suture wherein barb sizes are customized for each tissue layer will ensure maximum anchoring properties. In embodiments, the barbed suture(s) of the mesh obtained by the method of the invention may have both large and small barbs. Such barbed suture(s) with a combination of large and small barbs may be obtained by using monofilament yarns of a large diameter, for example ranging from 0.20 mm to 0.25 mm, for the first yarns which are threaded on the first guide bar B1, respectively for the sixth yarns which are threaded on the sixth guide bar B6, and monofilament yarns of a small diameter, for example ranging from 0.07 mm to 0.09 mm, for the second yarns which are threaded on the second guide bar B2, respectively for the fifth yarns which are threaded on the fifth guide bar B5, and monofilament yarns of a large diameter, for example ranging from 0.20 mm to 0.40 mm, for the third yarns which are threaded on the third guide bar B3, respectively for the fourth yarns which are threaded on the fourth guide bar B4.

All the yarns, namely the first, second, third, fourth, fifth and sixth yarns used for forming the knitted structure in the method of the invention are made of a biocompatible material. The biocompatible material may be identical or different from one yarn to another. The biocompatible material may be synthetic or natural. The biocompatible polymer material may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

The biocompatible material may be selected from the group consisting of biodegradable polymers, non-biodegradable polymers, and combinations thereof.

Non-biodegradable materials that may be used as biocompatible material for the yarns of the method of the invention include polyolefins, such as polyethylene, polypropylene, copolymers of polyethylene and polypropylene, and blends of polyethylene and polypropylene; polyamides (such as nylon); polyamines, polyimines, polyesters such as polyethylene terephthalate; polytetrafluoroethylene; polyether-esters such as polybutester; polytetramethylene ether glycol; 1,4-butanediol; polyurethanes; and combinations thereof. In other embodiments, non-degradable materials may include silk, collagen, cotton, linen, carbon fibers, titanium, and the like. The polypropylene may be isotactic polypropylene or a mixture of isotactic and syndiotactic or atactic polypropylene.

Biodegradable materials that may be used as biocompatible material of the yarns of the method of the invention include polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers of these materials and mixtures thereof.

In embodiments, the biocompatible material is selected from polyethylene, polypropylene, polyester such as polyethylene terephthalates, polyamide, silicone, polyether ether ketone (PEEK), polyarylether ether ketone (PAEK), polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

In embodiments, the biocompatible material used for the second and fifth yarns is polyethylene. The polyethylene may be a ultra high molecular weight polyethylene conferring to a multifilament yarn made therefrom a high tensile strength. In embodiments, the second and/or fifth yarns may be polyethylene multifilament yarns having a tensile strength ranging from about 25 cN/dTex to about 40 cN/dTex, for example a tensile strength of about 35 cN/dTex. Such polyethylene multifilament yarns made from ultra high molecular weight polyethylene and provided with such a tensile strength are commercially available from the company DSM under the tradename "Dyneema Purity®".

In embodiments, the biocompatible material used for the second and fifth yarns is polyethylene terephthalate. In embodiments, the second and fifth yarns may be polyethylene terephthalate multifilament yarns having a tensile strength ranging from about 25 cN/dTex to about 40 cN/dTex, for example a tensile strength of about 35 cN/dTex. In other embodiments, the second and fifth yarns may be high tenacity polyester yarns having a thickness ranging from 30 to 500 dTex, for example of 165 dTex.

In embodiments, the biocompatible material used for the first, third, fourth and/or sixth yarns is polypropylene. In embodiments, the first, third, fourth and/or sixth yarns are polypropylene monofilaments. Polypropylene may confer rigidity to the monofilaments and therefore to the barbs obtained therefrom.

The method of the invention allows customizing the elongate body and the barbs of the barbed suture(s) attached to the mesh in function of the contemplated surgical application. For example, if the barbed suture(s) is/are to be used to fix the mesh in skin or tendon, the barbs may be made relatively short and more rigid, for example by using polypropylene monofilament for the first, third, fourth and/or sixth yarns, to facilitate entry into this rather firm tissue. Alternatively, if the barbed suture(s) is/are intended for use in fatty tissue, which is relatively soft, the barbs may be made longer and spaced further apart to increase the ability of the suture(s) to grip the soft tissue.

In a second step, step b), of the method of the invention, the second knit portion is cut along the warp direction on both sides of said at least one weft stitched chain stitch and along an edge separating the second knit portion from the first knit portion, so as to remove the second knit portion from the knitted structure while maintaining said weft stitched chain stitch attached to the first knit portion.

In embodiments, where the knitting pattern followed by the first guide bar B1 during step a)ii) produces at least a partial weft in which said first yarns complete weft stitches with a plurality of chain stitches, thereby producing a plurality of weft stitched chain stitches, the cutting of step b) is repeated for each weft stitched chain stitch, thereby producing a plurality of barbed sutures attached to the first knit portion.

In embodiments where the warp knitting machine comprises a first needle-bed comprising first, second and third guide bars (B1, B2, B3) and a second needle-bed comprising fourth, fifth and sixth guide bars (B4, B5, B6) as described above, the cutting step b°) may comprise the following steps:

cutting the first needle-bed second knit portion along the warp direction on both sides of said at least one first weft stitched chain stitch and along an edge separating the first needle-bed second knit portion from the first bidimensional openworked knit, so as to remove the first needle-bed second knit portion from the knitted structure while maintaining said at least one first weft stitched chain stitch attached to the first bidimensional openworked knit, the second or third yarn forming part of said at least one first weft stitched chain stitch forming the elongate body of a first barbed suture attached to the first bidimensional openworked knit, the first yarns cuts extending from said weft stitches of said at least one first weft stitched chain stitch forming said barbs of said first barbed suture, cutting the second needle-bed second knit portion along the warp direction on both sides of said at least one second weft stitched chain stitch and along an edge separating the second needle-bed second knit portion from the second bidimensional openworked knit, so as to remove the second needle-bed second knit portion from the knitted structure while maintaining said at least one second weft stitched chain stitch attached to the second bidimensional openworked knit, the fourth or fifth yarn forming part of said at least one second weft stitched chain stitch forming the elongate body of a second barbed suture attached to the second bidimensional openworked knit, the sixth yarns cuts extending from said weft stitches of said at least one second weft stitched chain stitch forming said barbs of said second barbed suture.

In embodiments, said elongate body(ies) of said second barbed suture(s) is/are formed of fifth yarns only.

In embodiments, where the knitting pattern followed by the first guide bar B1 on the first needle-bed, respectively by the sixth guide bar B6 on the second needle-bed, during step a)ii), produces at least a partial weft in which said first yarns, respectively said sixth yarns, complete weft stitches with a plurality of chain stitches, thereby producing a plurality of first and second weft stitched chain stitches, the cutting of step b) is repeated for each of said first and second weft stitched chain stitches, thereby producing a plurality of first barbed sutures attached to the first bidimensional openworked knit, respectively a plurality of second barbed sutures attached to the second bidimensional openworked knit.

For each of such attached first and second weft stitched chain stitches, the chain stitch yarns, coming either from guide bar B2 (second yarns), B3 (third yarns), B4 (fourth yarns) and/or B5 (fifth yarns), preferably coming from guide bar B2 and/or guide bar B5, will form the elongate body of the thus obtained barbed sutures (first and/or second barbed sutures), and the first or sixth yarns cuts extending from the weft stitches of the first and second weft stitched chain stitches will form the barbs of the thus obtained barbed sutures (first and/or second barbed sutures).

In embodiments, the cutting step may be performed on line, namely while the knitted structure produced at step a) is still on the knitting machine. For example, the knitting machine may be provided with adequate blades. Alternatively, the cutting step may be performed off line, for example with pairs of scissors. For example, the cutting step may be performed by LASER cutting, high frequency welding cutting, roller cutting and/or hot resistance cutting.

In embodiments where the first and/or sixth yarns are monofilaments, the cutting step may be performed via melting the monofilaments at a temperature above their melting point so as to cut said monofilaments. Such a cutting step may be performed on line or off line.

In embodiments where the knitting machine used in the method of the invention comprises two needle-beds and six guide bars are used as described above, after the cutting step b) as described above, the knitted structure is then opened so as to spread in a single plane the part of the knitted structure obtained from the first needle-bed and the part of the knitted structure obtained from the second needle-bed, wherein the first bidimensional openworked knit, the connecting knit portion, and the second bidimensional openworked knit form altogether the mesh; the second or third yarn forming part of said at least one first weft stitched chain stitch forms the elongate body of a first barbed suture attached to the first bidimensional openworked knit, the first yarns cuts extending from said weft stitches of said at least one first weft stitched chain stitch forming said barbs of said first barbed suture; the fourth or fifth yarn forming part of said at least one second weft stitched chain stitch forms the elongate body of a second barbed suture attached to the second bidimensional openworked knit, the sixth yarns cuts extending from said weft stitches of said at least one second weft stitched chain stitch forming said barbs of said second barbed suture.

In embodiments, for example when "y" is greater than 2, linking yarns from the three-dimensional openworked knit obtained in step a)0) may be cut along stitches ranging from 2 to y, such a step taking place after the cutting step b) described above and before opening the knitted structure in a single plane. The purpose of such a step is to reduce the height of the connecting knit portion in the final configuration of the mesh, when it is spread in a single plane, in order to avoid generating an extra thickness in the middle of the mesh.

After cutting step b) of the method of the invention, the first and/or sixth yarns cuts forming the barbs may generally extend substantially radially out of the chain stitch yarn forming the elongate body of the barbed suture along an angle between the first and/or sixth yarns cuts and the chain stitch yarn of about 90°. In the present application, the angle between the first and/or sixth yarns cuts and the yarn forming the elongate body is measured with a Profile Projector ORAM 300V geometric.

The angle between the first and/or sixth yarns cuts and the yarn forming the elongate body may be modified by submitting the attached barbed suture to a stretching treatment. For example, the angle between the first and/or sixth yarns cuts and the yarn forming the elongate body may be modified so that said angle reaches 45°, 35°, or 33°. The method of the invention therefore allows selecting the adequate angle between the barbs and the elongate body of the barbed suture for an optimized fixation in the biological tissues.

In embodiments, the method further comprises a stretching step during which the second knit portion produced in step a)ii) and/or the attached barbed suture(s) obtained in step b°) is(are) submitted to a stretching treatment. The stretching treatment may comprise a step of stretching the second knit portion or the attached barbed suture(s) in the warp direction. For example, the stretching treatment may be performed by using a traction testing machine such as Hounsfield model H5KS in which a first end of the second knit portion or the first end of an attached barbed suture is grasped by a fixed jaw of the machine and the opposite end of the second knit portion or of the attached barbed suture is grasped by a moving jaw. By moving away from the fixed jaw, the moving jaw stretches the second knit portion or the attached barbed suture.

On an industrial scale, the stretching treatment of the second knit portion in the warp direction may be performed on a heat-setting machine for example. By stretching the second knit portion in the warp direction, all weft stitched chain stitch(es) of the second knit portion are stretched, and as a consequence, all the attached barbed sutures are stretched.

In embodiments, the attached barbed suture(s) is/are stretched from about 0% to about 90%, which means that the stretched attached barbed suture(s) show(s) a length from about 0% to about 90% greater than the initial length of the attached barbed suture.

In embodiments, the second knit portion and/or the attached barbed suture(s) are stretched at 40%, which means that each of the second knit portion and/or the attached barbed suture(s) shows a length 40% greater than their initial length for each. Such a stretching step of 40% may result in the angle between the first and/or sixth yarns cuts and the yarn forming the elongate body be modified to reach about 45°. Such an angle between the first and/or sixth yarns cuts and the yarn forming the elongate body of the barbed suture may be desirable for barbed sutures intended to be used in soft biological tissues.

In other embodiments the second knit portion and/or the attached barbed suture(s) are stretched at 80%, which means that each of the second knit portion and/or the attached barbed suture(s) shows a length 80% greater than their initial length for each. Such a stretching step of 80% may result in the angle between the first and/or sixth yarns cuts and the yarn forming the elongate body be modified to reach about 35°. Such an angle between the first and/or sixth yarns cuts and the yarn forming the elongate body of the barbed suture may be desirable for barbed sutures intended to be used for anchoring purposes in dense biological tissues such as muscles.

In other embodiments the second knit portion and/or the attached barbed suture(s) are stretched at 90%, which means that each of the second knit portion and/or the attached barbed suture(s) shows a length 90% greater than their initial length for each. Such a stretching step of 90% may result in the angle between the first and/or sixth yarns cuts and the yarn forming the elongate body be modified to reach about 33°. Such an angle between the first and/or sixth yarns cuts and the yarn forming the elongate body of the barbed suture may be desirable for barbed sutures intended to be used for anchoring purposes in dense biological tissues such as muscles.

In embodiments, the attached barbed suture(s) may be submitted to a twisting treatment, for example for giving to the barbs a helical pattern. Such a treatment may be performed with a rotor machine.

In embodiments, the method of the invention further comprises a heat-setting step during which either the second knit portion produced in step a)ii) or the attached barbed suture(s) resulting from step b) is(are) submitted to a heat-setting treatment. The heat-setting treatment is intended to fix the barbed suture in the desired configuration. The heat-setting step may take place either between step a) and b), namely before the cutting step, or after step b), namely after the cutting step. For example, in case the second knit portion or the attached barbed suture(s) are submitted to a stretching treatment and/or a twisting treatment, they may simultaneously be submitted to a heat-setting treatment, so that the barbs configuration regarding for example the angle made between the first and/or sixth yarns cuts and the elongate body and/or the helical pattern obtained by the twisting treatment are fixed.

The heat-setting treatment may comprise a step of heating the second knit portion or the attached barbed suture(s) at a temperature ranging from 30° C. to 230° C. during a time period ranging from 1 min to 4 min. The heat-setting treatment may be performed on a heat-setting machine.

The mesh having one or more barbed suture(s) attached thereto obtained by the method of the invention may be sterilized by any means within the purview of those skilled in the art.

The barbed suture(s) of the mesh obtained by the method of the invention may be coated or impregnated with one or more medico-surgically useful substances which accelerate or beneficially modify the healing process when the barbed suture(s) is/are applied to a surgical site. In certain embodiments, the coating may be formed from biodegradable polymers selected from the group consisting of lactones, carbonates, polyorthoesters, hydroxyalkoanates, hydroxybutyrates, bioactive agents, polyanhydrides, silicone, calcium stearoyl lactylates, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial and tend to promote the healing process. For example, the barbed suture(s) of the mesh obtained by the method of the invention can be provided with a bioactive agent that will be deposited at the sutured site. The bioactive agent can be chosen for its antimicrobial properties, capability for promoting wound repair and/or tissue growth, or for specific indications such as thrombosis.

The barbed suture(s) of the mesh obtained by the method of the invention may additionally comprise a needle at their free end. The needle attachment may be made by any conventional method such as crimping, swaging, and the like.

The prosthetic mesh having one or more barbed suture(s) attached thereto obtained by the method of the invention may be utilized in any open endoscopic or laparoscopic methods. For example, the prosthetic mesh having one or more barbed suture(s) attached thereto obtained by the method of the invention may be utilized for the treatment of hernia.

For example, the mesh obtained by the method of the invention may play its function of abdominal wall repair while the one or more barbed sutures attached thereto may be used by the surgeon in order to fix the mesh to the abdominal wall. The surgeon does not have to look for sutures at the time he needs to fix the mesh to the biological tissue. Moreover, because of the barbed nature of the suture(s) attached to the mesh, the surgeon needs not perform surgical knots. The barbs of the attached barbed suture(s) perform the anchoring function of the suture into the biological tissue very efficiently.

BRIEF DESCRIPTION OF THE SEVERAL VIEWS OF THE DRAWING

The advantages of the method of the invention will appear more clearly from the following examples and attached drawings in which.

DETAILED DESCRIPTION OF THE INVENTION

EXAMPLES

Example 1

In the present example, a prosthetic mesh 1 (see FIG. 4) having an attached barbed suture 10 attached thereto is formed according to the method of the invention, using on needle-bed only.

In a first step, step a°), a knitted structure 2 (see FIG. 1) is produced on a Raschel machine comprising one needle-bed comprising a first guide bar B1, a second guide bar B2 and a third guide bar B3. The knitted structure is produced on a determined length along the warp direction corresponding to a total number N of 70 stitches, with x=30.

In other embodiments, the knitted structure could be produced on other lengths corresponding to other number of stitches.

In the present example, all the knitting patterns are given according to the ISO 11676 standard (publication year 2014).

Figure 1:
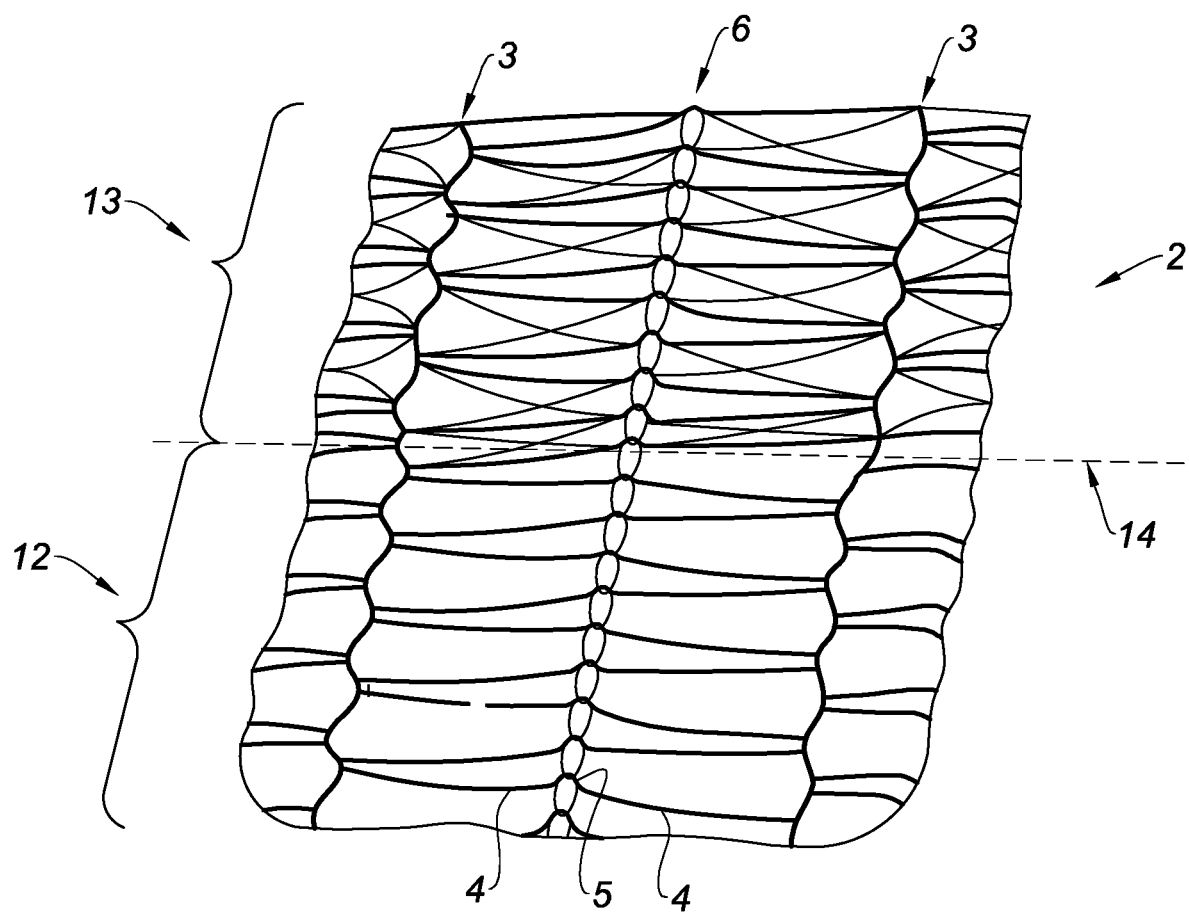
FIG. 1 is a schematic top view showing an embodiment of the knitted structure obtained in step a) of the method of the invention in the case where one needle-bed is used.

With reference to FIG. 1, is shown schematically a piece of the knitted structure 2, with the first knit portion 13 and the second knit portion 12, and the edge 14 separating the first knit portion 13 from the second knit portion 12. The knitted structure 2 is produced as described below.

In a step a)i), the first knit portion 13 capable of favoring cellular growth is produced for stitches ranging from 1 to 30.

The knitting pattern followed by bars B1, B2 and B3 is the following one:
Bar B1: (5.4/3.2/0.1)×10//
Bar B2: (5.4/3.2/0.1)×10//
Bar B3: (0.1/2.3/5.4)×10//

In a step a)ii), thr second knit portion 12 is produced for stitches ranging from 31 to 70.

The knitting pattern followed by bars B1, B2 and B3 is the following one:
Bar B1: (0.0/2.3/5.5/3.2)×10//
Bar B2: (2.3/2.3/3.2/3.2)×10//
Bar B3: (2.3/2.3/3.2/3.2)×10//

In both steps a)i) and aii), B1 is threaded 1 full, 3 empty, B2 is threaded 1 full, 3 empty and B3 is threaded 1 full, 3 empty, along the whole width of the machine.

Such a pattern results in a distance between a weft stitched chain stitch and the two adjacent chain stitches of about 3.5 mm.

The yarns threaded in guide bar B1 (first yarns) are polypropylene monofilaments having a diameter of 0.20 mm.

The yarns threaded in guide bar B2 (second yarns) are multifilament yarns of ultra high molecular weight polyethylene, such as those marketed by the company DSM under the tradename "Dyneema Purity®". These multifilaments have a tensile strength of 35 cN/dTex.

The yarns threaded in guide bar B3 (third yarns) are polypropylene monofilaments having a diameter of 0.30 mm.

Figure 2:
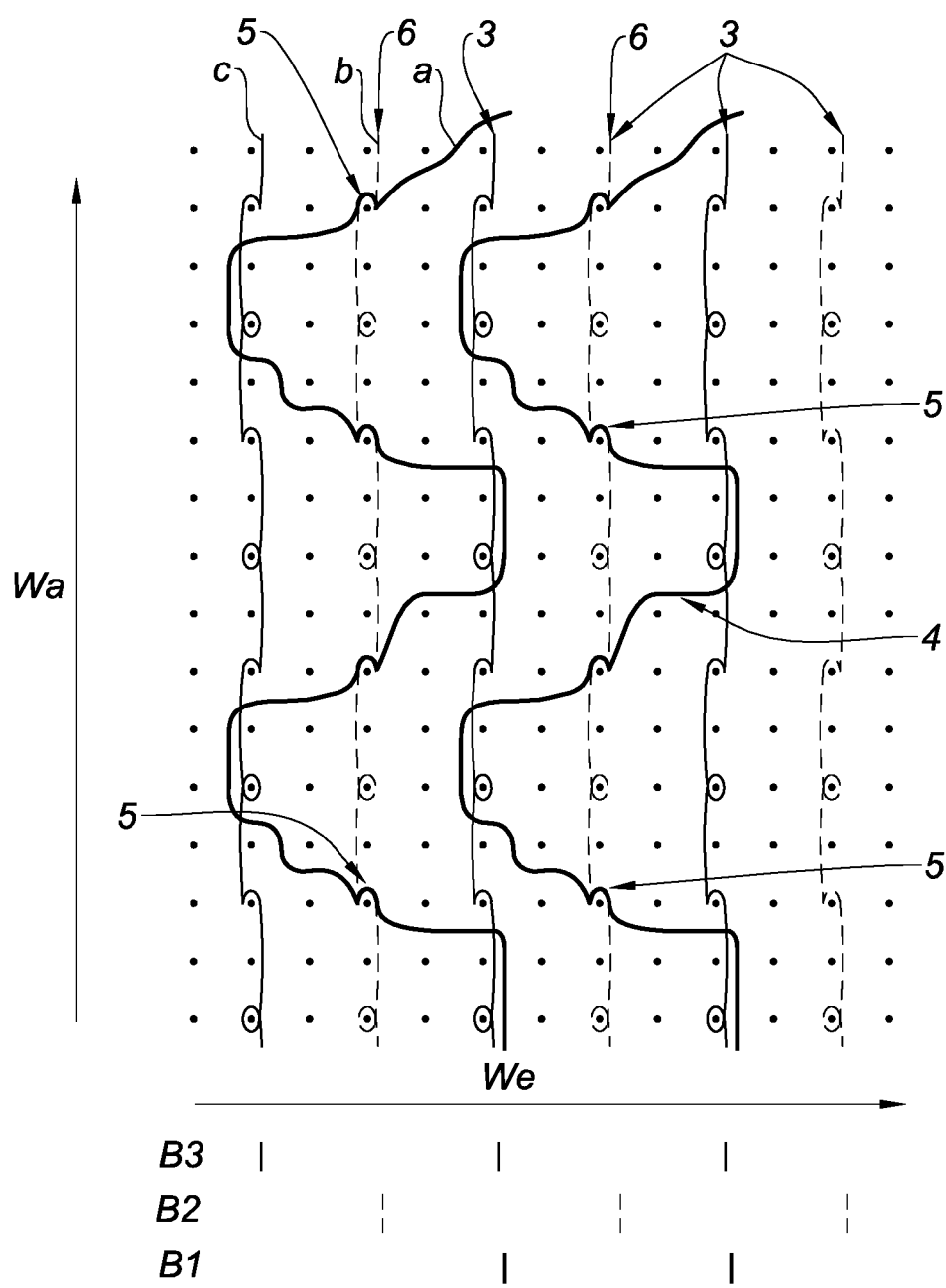
FIG. 2 is a schematic view showing an embodiment of a knitting pattern suitable for the knitting process of step a°)ii) of the method of the invention in the case where one needle-bed is used such as in FIG. 1.

With reference to FIG. 2 showing the knitting pattern of step a)ii) above in accordance with a representation well known for one skilled in the art, are shown the warp direction Wa, the weft direction We, the first yarns "a" (threaded in guide bar B1) shown as a thick line, the second yarns "b" (threaded in guide bar B2) shown as a dotted line, and the third yarns "c" (threaded in guide bar B3) shown as a thin line. The knitting pattern produces a plurality of chain stitches 3 (with second and third yarns (b, c) coming from guide bars B2 and B3) and a partial weft 4 (with first yarns "a" coming from guide bar B1). The first yarns "a" complete weft stitches 5 with some of the chain stitches 3, herein after called weft stitched chain stitches 6. Actually, as appears from FIG. 2, the knitting pattern produces one weft stitched chain stitch 6 out of two chain stitches 3 present in the second knit portion 12. In the present example, it happens that the weft stitched chain stitches 6 correspond to all the chain stitches 3 that are made with the second yarns "b". In other embodiments not shown, the weft stitched chain stitches 6 could correspond to the chain stitches 3 that are made with the third yarns "c", or could correspond to some of the chain stitches made with the second yarns "b" or with the third yarns "c". In the present example, the distance between two adjacent weft stitched chain stitches 6 is due to the threading-in of the second guide bar B2, which is 1 full, 3 empty. Such a threading-in may result in a distance between the weft stitched chain stitches 6 of about 3.5 cm.

Figure 3:
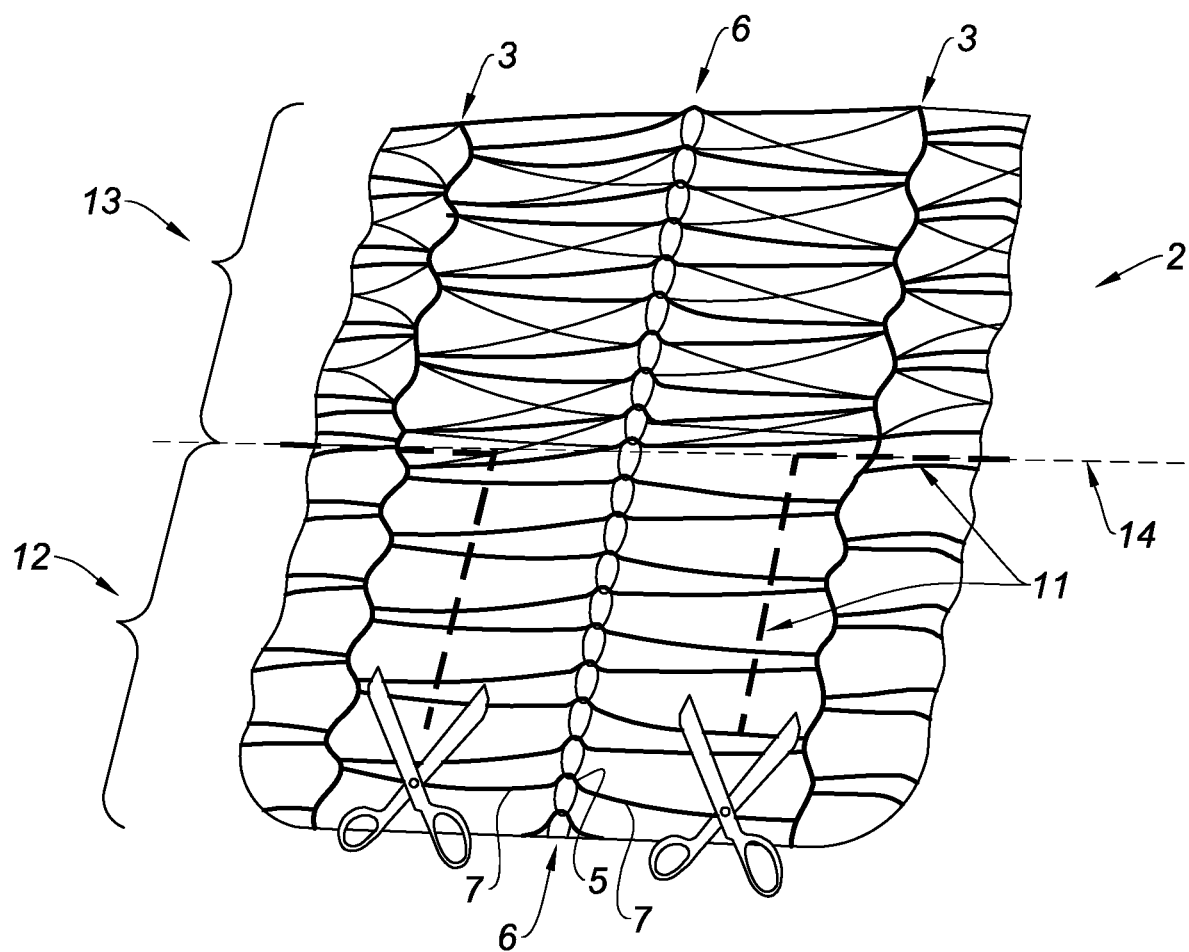
FIG. 3 is a schematic view showing the cutting step of the method of the invention for the knitted structure of FIG. 1.

With reference to FIG. 3, in a second step, step b°), the second knit portion 12 thus produced is cut along the warp direction on both sides of the weft stitched chain stitches 6 and along the edge 14 separating the second knit portion 12 from the first knit portion 13 along cutting lines 11, so as to remove the second knit portion 12 from the knitted structure 2 while maintaining the weft stitched chain stitch 6 attached to the first knit portion 13. The cutting step may be performed for example with a pair of scissors.

For sake of clarity, the figures show the cutting step for one weft stitched chain stitch 6 only. Anyway, the cutting step may be repeated for each weft stitched chain stitch 6 present on the width of the knitted structure 2 corresponding to the desired width of the final mesh 1 to be obtained.

Figure 4:
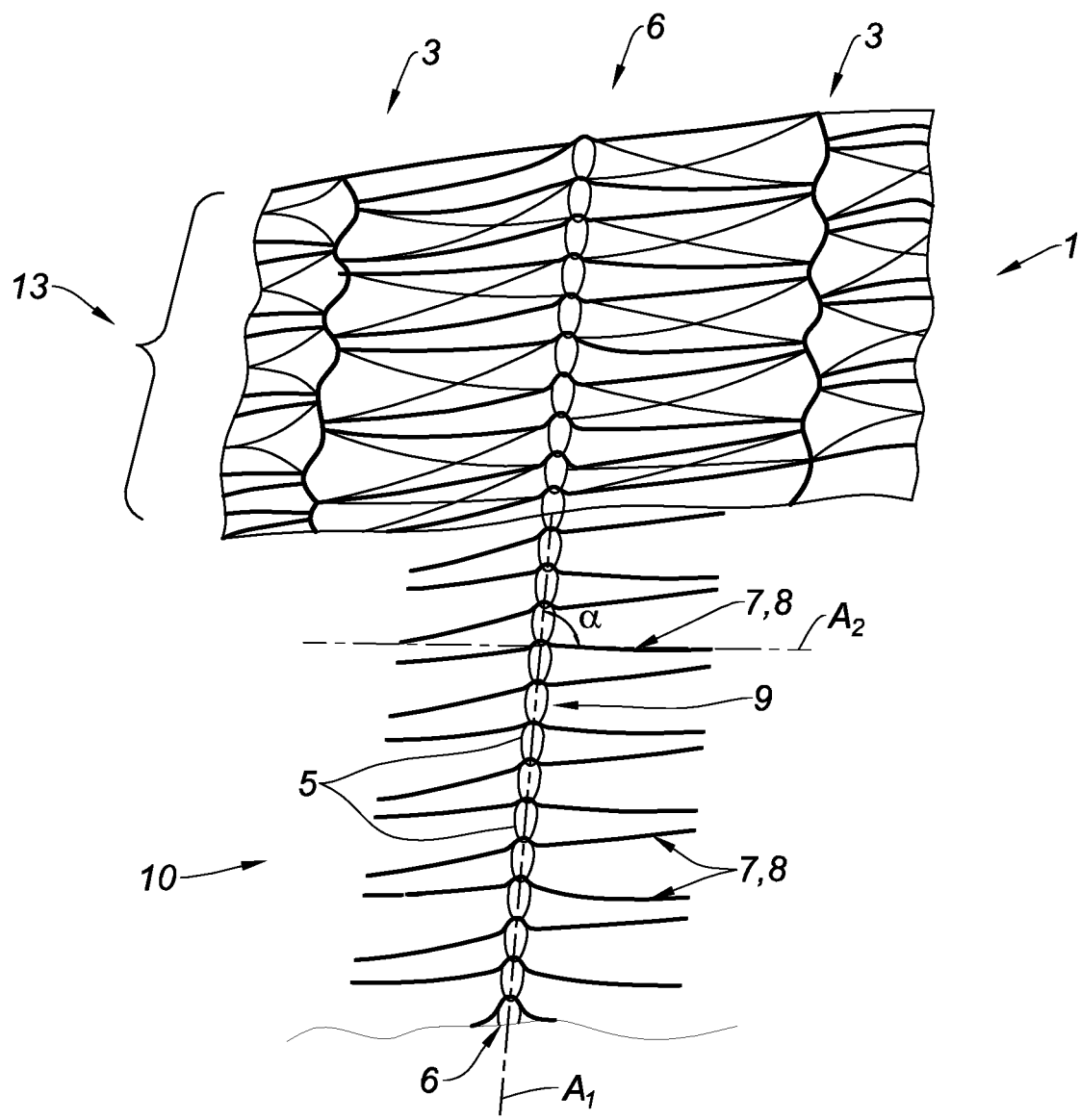
FIG. 4 is a schematic top view showing a mesh having a barbed suture attached thereto obtained after performing step b°) of the method of the invention on the knitted structure of FIG. 1.

FIG. 4 shows the mesh 1 having an attached barbed suture 10 obtained in the present example with the method of the invention, with the first knit portion 13 forming the mesh and the attached weft stitched chain stitch 6, in which the chain stitch yarn (second yarn "b" with reference to FIG. 2) of the weft stitched chain stitch 6 forms the elongate body 9 of the barbed suture 10 and the monofilament cuts 7 coming from first yarns "a" and extending from the weft stitches 5 of the weft stitched chain stitch 6 form the barbs 8 of the barbed suture 10.

As shown on this Figure, the attached weft stitched chain stitch 6 which is also the elongate body 9 of the attached barbed suture 10 extends along a longitudinal axis A1, and the monofilament cuts 7, which are also the barbs 8, each extend along a longitudinal axis A2. On FIG. 4, the angle α between axis A1 and axis A2 is substantially about 90°.

As appears from the cutting step shown on FIG. 3, the length of the monofilament cuts 7, and therefore of the barbs 8, depend both on the initial distance between the weft stitched chain stitch 6 and adjacent chain stitches 3, and on the location of the cutting lines 11.

Although FIG. 4 shows the mesh 1 with only one attached barbed suture 10, a plurality of attached barbed sutures 10 could be obtained depending on the number of weft stitched chain stitches 6 cut along the width of the knitted structure 2 corresponding to the desired width of the final mesh 1 to be obtained.

Figure 6:
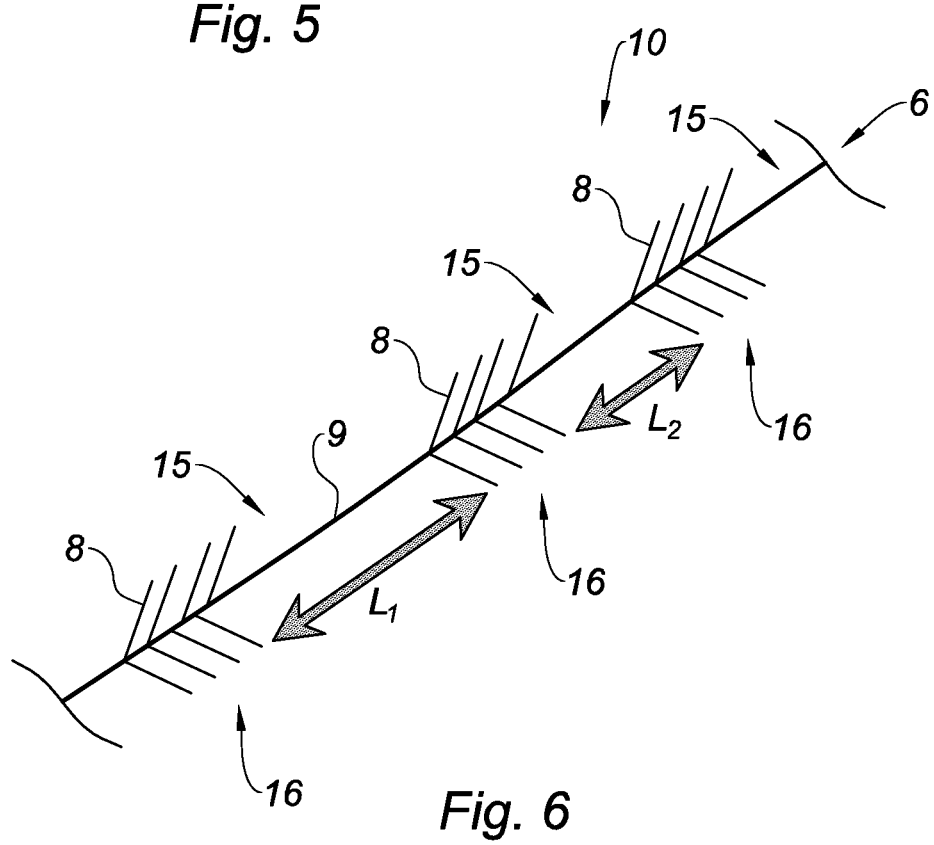
FIG. 6 is a partial schematic view of an attached barbed suture obtained after step b°) of the method of the invention having active and passive portions along its length.

With reference to FIG. 6 is shown schematically a portion of an attached barbed suture 10 obtained according to the method of the present example in the case where the first guide bar B1 was fed intermittently with the first yarns. During the time periods for which the guide bar B1 was not fed with the first yarns, no weft stitches were produced on the weft stitched chain stitch 6, thereby resulting in portions of the weft stitched chain stitch 6 free of barbs, namely passive portions 15. An attached barbed suture 10 having alternating active portions 16 (when guide bar B1 was fed with first yarns) and passive portions 15 is therefore obtained. As shown on this Figure, the respective distances (L1, L2) between two adjacent active portions 16 may vary, as such distances are dependent on the time period during which the guide bar B1 was not fed.

Figure 5:
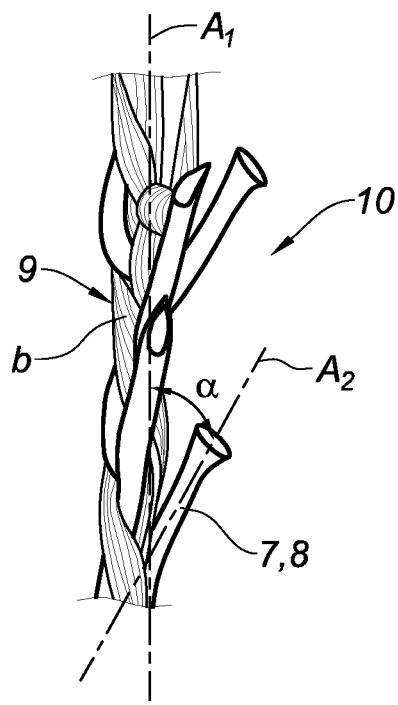
FIG. 5 is a partial front view of an attached barbed suture obtained by the method of the invention showing the angle formed between the barbs and the elongate body of the suture.

With reference to FIG. 5 is shown a larger view of a portion of the attached barbed suture 10 of FIG. 4 after a stretching treatment in which the attached barbed suture was stretched at 90%. As appears from this Figure, after the stretching treatment, the angle α between axis A1 and axis A2, in other words between the yarn "b" forming the elongate body 9 of the barbed suture 10 and the monofilament cuts 7, also barbs 8, has been modified and is now about 33°.

The attached barbed suture 10 of FIG. 5 is then submitted to a heat-setting treatment in order to fix the configuration of the barbs 8 with respect to the elongate body 9 of the suture 10.

In embodiments not shown, the knitting pattern used in step a)ii) above may result in all chain stitches being also weft stitched chain stitches, when the first yarns produce weft stitches with all chain stitches produced by the second and the third guide bars. In other embodiments, the knitting pattern may produce only one weft stitched chain stitch out of three, four, five, etc. . . . chain stitches present in the second knit portion, which may result in variations of the distance between two adjacent weft stitched chain stitches. Alternatively, this distance may vary due to different threading-in of the guide bars.

The mesh 1 with the barbed suture 10 attached thereto may be particularly useful in hernia repair. The mesh may play its function of abdominal wall repair while the one or more barbed sutures 10 attached thereto may be used by the surgeon in order to fix the mesh to the abdominal wall. The surgeon does not have to look for sutures at the time he needs to fix the mesh to the biological tissue. Moreover, because of the barbed nature of the suture(s) attached to the mesh, the surgeon needs not perform surgical knots. The barbs of the attached barbed suture(s) perform the anchoring function of the suture into the biological tissue very efficiently.

Example 2

In the present example, a prosthetic mesh 28 having a plurality of barbed sutures (10; 10') attached thereto (see FIG. 12) is formed according to the method of the invention using two needle-beds. The knitting machine used may be a Raschel knitting machine comprising a double needle-bed. The description of the method used in the present example is made with reference to FIGS. 7-12.

The Raschel knitting machine comprises a first needle-bed comprising three guide bars B1, B2 and B3 and a second needle-bed comprising three guide bars B4, B5 and B6. In the present example, the same references that are used for the production and steps performed in relation to the first needle-bed will be maintained for the production and steps performed in relation to the first needle-bed, but with a "prime" indicated after the reference digit.

In the present example, all the guide bars (B1, B2, B3, B4, B5, B6) are threaded 1 full, 3 empty along the whole width of the machine and all the knitting patterns are given according to the ISO 11676 standard (publication year 2014).

In the present example:
first guide bar B1 is threaded with first yarns and sixth guide bar B6 is threaded with sixth yarns, the first and sixth yarns being monofilaments of polypropylene having a diameter of about 0.20 mm,
second guide bar B2 is threaded with second yarns, and fifth guide bar B5 is threaded with fifth yarns, the second and fifth yarns being multifilaments of high tenacity polyester having a thickness of 165 dTex,
third guide bar B3 is threaded with third yarns and fourth guide bar B4 is threaded with fourth yarns, the third and fourth yarns being monofilaments of polypropylene having a diameter of about 0.30 mm.

In a first step a), a knitted structure 27 (see FIG. 7) is produced on a length in the warp direction Wa corresponding to a number N of 70 stitches, with x=30 and y=6. The warp direction Wa is indicated on FIG. 7. Although this warp direction is not repeated for FIGS. 8-10 for sake of clarity, it is identical for these Figures as in FIG. 7.

1°) During step a)0): for stitches ranging from 1 to 6, a connecting portion 20 is produced under the form of a three-dimensional openworked knit 21 capable of favoring cellular growth, according to the following knitting pattern:
B1: (5.4.3.3/3.2.1.1/0.1.3.3)×2//
B2: (5.4.3.3/3.2.1.1/0.1.3.3)×2//
B3: 0.1.0.1/2.3.2.3/5.4.2.2/0.1.2.2/2.3.4.4/5.4.2.2//
B4: 0.1.0.1/2.3.2.3/4.4.5.4/2.2.0.1/2.2.2.3/4.4.5.4//
B5: (3.3.5.4/3.3.3.2/1.1.0.1)×2//
B6: (3.3.5.4/3.3.3.2/1.1.0.1)×2//

The above knitting pattern allows producing a knit that has a first face produced on the first needle-bed by the first, second and third yarns from the first, second and third guide bars (B1, B2, B3), and a second face, produced on the second needle-bed by the fourth, fifth and sixth yarns from the fourth, fifth and sixth guide bars (B4, B5, B6), the first and second faces being linked together by some of the third and/or fourth, yarns crossing from the first needle-bed to the second needle-bed and vice-versa, thereby forming linking yarns.

2°) During step a)i): for stitches ranging from 7 to 30: a first knit portion 22 is produced. During this step and the subsequent step, independent knits are produced on each of the needle bed in parallel.

On the first needle-bed, a first bidimensional openworked knit 23 capable of favoring cellular growth is produced according to the following knitting pattern:
B1: (5.4.3.3/3.2.1.1/0.1.3.3)×8//
B2: (5.4.3.3/3.2.1.1/0.1.3.3)×8//
B3: (0.1.2.2/2.3.4.4/5.4.2.2)×8//

On the second needle-bed, a second bidimensional openworked knit 23' capable of favoring cellular growth is produced according to the following knitting pattern:
B4: (2.2.0.1/2.2.2.3/4.4.5.4)×8//
B5: (3.3.5.4/3.3.3.2/1.1.0.1)×8//
B6: (3.3.5.4/3.3.3.2/1.1.0.1)×8//

The first and second bidimensional openworked knits being independent from each other. They each constitute a bidimensional knit suitable for use as a reinforcement member for the repair of hernia in the abdominal wall.)

3°) During step a)ii): for stitches ranging from 31 to 70: a second knit portion 24 is produced.

On the first needle-bed, a first needle-bed second knit portion 25 is produced according to the following knitting pattern:
B1: (0.0.0.0/2.3.4.4/5.5.5.5/3.2.1.1)×10//
B2: (2.3.2.2/2.3.3.3/3.2.3.3/3.2.2.2)×10//
B3: (2.3.2.2/2.3.3.3/3.2.3.3/3.2.2.2)×10//

In a similar way as described in Example 1 for the second knit portion 12, in the present example, the knitting pattern followed by the second and third guide bars (B2, B3) produces chain stitches and the knitting pattern followed by the first guide bar B1 produces a partial weft in which said first yarns complete weft stitches with a plurality, four in the example shown in the Figures, of said chain stitches, thereby producing a plurality of weft stitched chain stitches 6, four in the example shown.

On the second needle-bed, a second needle-bed second knit portion 25' is produced according to the following knitting pattern:
B4: (2.2.2.3/2.2.2.3/3.3.3.2/3.3.3.2)×10//
B5: (2.2.2.3/2.2.2.3/3.3.3.2/3.3.3.2)×10//
B6: 1.1.0.0/0.0.2.3/4.4.5.5/5.5.3.2)×10//

Similarly to what takes place for the first-needle bed, the knitting pattern followed by the fourth and fifth guide bars (B4, B5) produces chain stitches and the knitting pattern followed by the sixth guide bar B6 produces a partial weft in which the sixth yarns complete weft stitches with a plurality, four as shown on the Figures, of said chain stitches, thereby producing a plurality of weft stitched chain stitches, for example four weft stitched chain stitches 6'.

Figure 7:
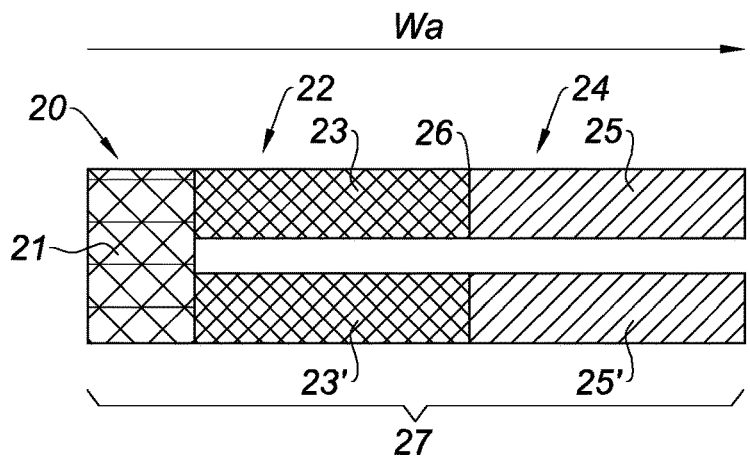
FIG. 7 is a schematic side view showing the knitted structure obtained in step a) of the method of the invention in the case where two needle-beds are used.
Figure 8:
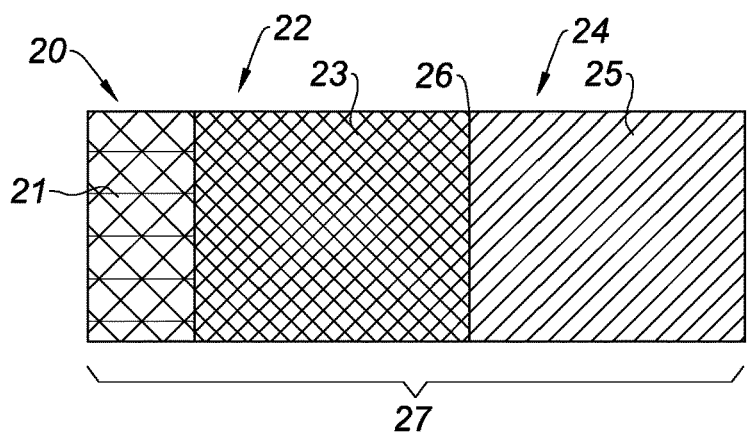
FIG. 8 is a schematic top view of the knitted structure of FIG. 7.
Figure 9:
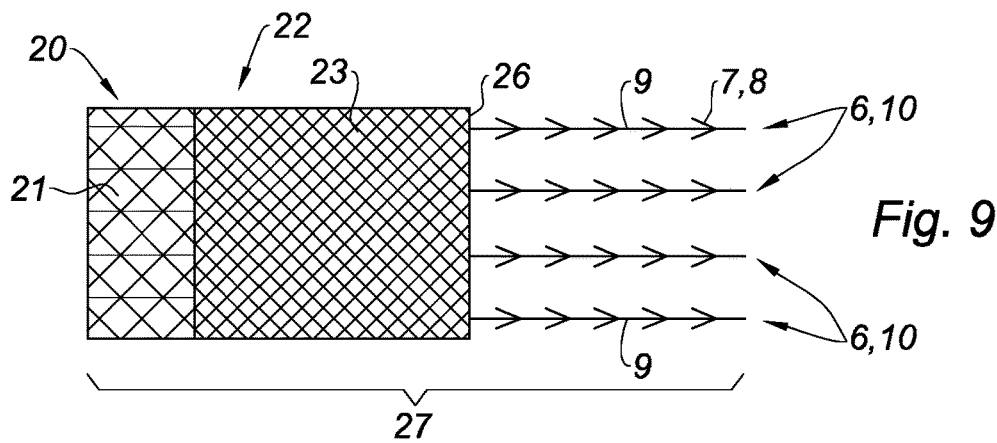
FIG. 9 is a schematic top view of the knitted structure of FIG. 7 after cutting step b°)

The knitted structure 27 produced in the step a) above is shown on FIGS. 7 and 8 which are schematic side view and bottom view of the knitted structure.

In a step b°), with reference to FIGS. 9-12:
the first needle-bed second knit portion 25 is cut along the warp direction on both sides of each of the four weft stitched chain stitches 6 obtained by first, second and third guide bars (B1, B2, B3) and along an edge 26 separating the first needle-bed second knit portion 25 from the first bidimensional openworked knit 23, so as to remove the first needle-bed second knit portion 25 from the knitted structure 27 while maintaining the four weft stitched chain stitches 6 attached to the first bidimensional openworked knit 23, the second needle-bed second knit portion 25' is cut along the warp direction on both sides of each of the four weft stitched chain stitches 6' obtained by third, fourth and fifth guide bars (B4, B5, B6) and along an edge 26' separating the second needle-bed second knit portion 25' from the second bidimensional openworked knit 23', so as to remove the second needle-bed second knit portion 25' from the knitted structure 27 while maintaining the four weft stitched chain stitches 6' attached to the second bidimensional openworked knit 23'.

The cutting step is performed in the same manner as described in Example 1.

Figure 10:
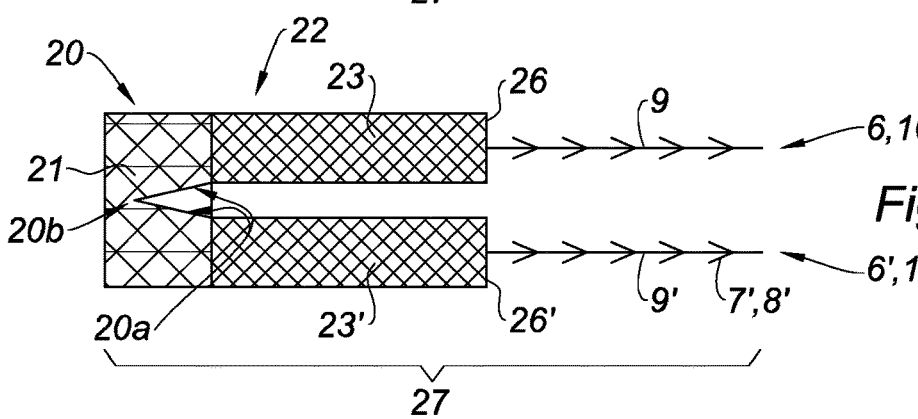
FIG. 10 is a schematic side view showing optional step c°)

In a step c°), with reference to FIG. 10, the linking yarns from the three-dimensional openworked knit 21 obtained in step a)0) are cut along stitches ranging from 2 to 6. As a result, the connecting knit portion 20 comprises a cut part 20a and a bridge part 20b, said bridge part 20b connecting the part of the knitted structure 27 obtained on the first needle-bed to the part of the knitted structure 27 obtained on the second needle-bed.

This step may be optional, for example in the case where the connecting knit portion 20 extends already on a length corresponding to 2 stitches only from the start. The purpose of this step c°) is to reduce the height of the connecting knit portion in the final configuration of the mesh as shown in FIG. 11, in order to avoid generating an extra thickness in the middle of the mesh 28.

If the number of stitches in the warp direction along which the connecting knit portion extends from the start is low enough for not producing any extra thickness in the final configuration of the mesh, than the present step c°) is unnecessary.

Figure 11:
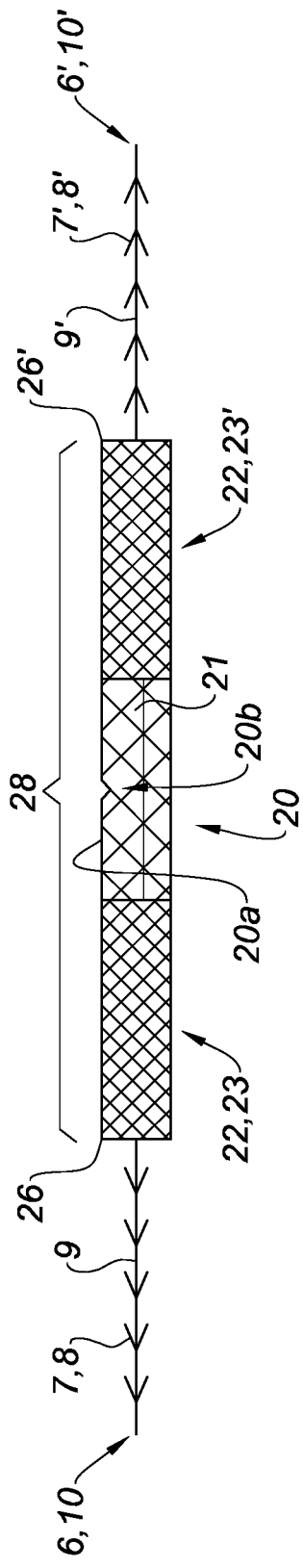
FIG. 11 is a side view of the prosthetic mesh of the invention obtained from the knitted structure of FIG. 7 after step d°)
Figure 12:
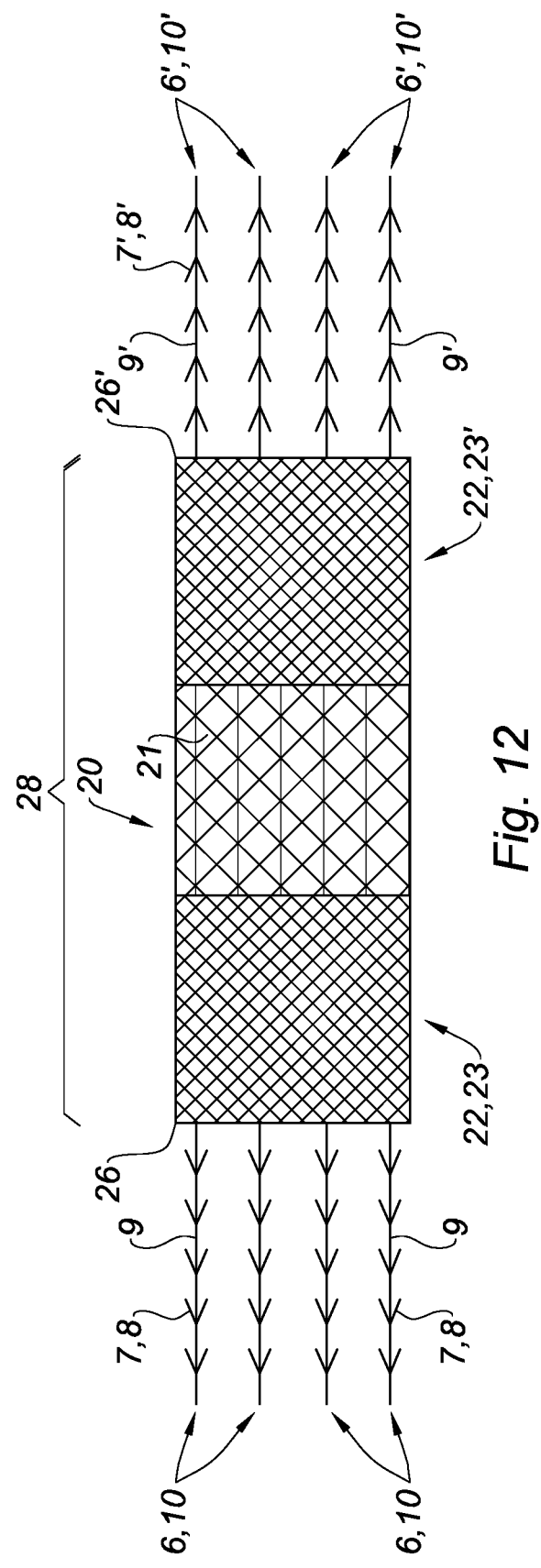
FIG. 12 is a top view of the prosthetic mesh of the invention obtained from the knitted structure of FIG. 7 after step d°).

In a step d°), the knitted structure 27 is opened so as to spread in a single plane the part of the knitted structure obtained from the first needle-bed and the part of the knitted structure obtained from the second needle-bed as shown on FIGS. 11 and 12.

With reference to FIGS. 11 and 12, the first bidimensional openworked knit 23, the connecting knit portion 20, cut according to step c°), and the second bidimensional openworked knit 23' form altogether the mesh 28: this mesh 28 is made of knits capable of favoring cellular growth and is therefore particularly indicated for repair of the abdominal wall for example. The second yarns forming part of the weft stitched chain stitches 6 obtained by first, second and third guide bars (B1, B2, B3) form the elongate body 9 of first barbed sutures 10 attached to the first bidimensional openworked knit 23, the monofilament cuts 7 of first yarns extending from the weft stitches of the weft stitched chain stitches 6 form the barbs 8 of the first barbed sutures 10; the fifth yarns forming part of the weft stitched chain stitches 6' obtained by fourth, fifth and sixth guide bars (B4, B5, B6) form the elongate body 9' of second barbed sutures 10' attached to the second bidimensional openworked knit 23', the monofilament cuts 7' of sixth yarns extending from the weft stitches of the weft stitched chain stitches 6' form the barbs 8' of the second barbed sutures 10'.

In the present example, the elongate bodies 9 of the first barbed sutures 10 are formed of second yarns only and the elongate bodies 9' of the second barbed sutures 10' are formed of fifth yarns only.

In other embodiments not shown, the elongate bodies 9 of the first barbed sutures 10 may be formed of third yarns only or of a combination of second and third yarns, and the elongate bodies 9' of the second barbed sutures 10' may be formed of fourth yarns only or of a combination of fourth and fifth yarns.

The mesh 28 having barbed sutures (10, 10') attached thereto as obtained in the present example may be particularly useful in hernia repair. The mesh 28 may play its function of abdominal wall repair while the barbed sutures (10, 10') attached thereto may be used by the surgeon in order to fix the mesh 28 to the abdominal wall. The surgeon does not have to look for sutures at the time he needs to fix the mesh to the biological tissue. Moreover, because of the barbed nature of the suture(s) (10, 10') attached to the mesh 28, the surgeon needs not perform surgical knots. As appears from FIGS. 11 and 12, the barbs (8, 8') of the attached barbed suture(s) (10, 10') are naturally oriented in opposite direction, thereby performing efficiently their anchoring function of the suture (10; 10') and of the mesh 28 into the biological tissue.

In addition, the attached barbed sutures (10; 10') of the mesh 28 may be further submitted to a treatment, such as a stretching treatment, a twisting treatment, a heat-setting treatment and/or a combination of these treatments, so as to provide them with an optimized configuration in function of the intended use of the mesh and sutures, in order to ensure an optimized fixation of the mesh in the biological tissues.

The method of the invention allows preparing prosthetic meshes having one or more barbed suture(s) attached thereto in a very simple way, and in only one single knitting process. The method further allows adapting very easily and in a cost effective manner the nature and structure of the attached barbed suture(s), such as frequency per cm, configuration, spacing, length and surface area of the barbs, depending upon the tissue in which the barbed suture(s) are to be used. With the method of the invention, it is possible to obtain meshes having barbed suture(s) attached thereto, with barbed suture(s) in which the barbs may be arranged in any suitable pattern, for example, helical, linear, or randomly spaced.

The invention claimed is:

1. A method for forming a prosthetic mesh having at least one barbed suture attached thereto, said barbed suture comprising an elongate body provided with barbs extending substantially radially out from said elongate body, said method comprising the following steps:
   a) producing a knitted structure on a warp knitting machine comprising at least one needle-bed comprising at least three guide bars, a first guide bar B1 a second guide bar B2 and a third guide bar B3, said first guide bar B1 being threaded with first yarns of a biocompatible material, said second guide bar B2 being threaded with second yarns of a biocompatible material, said third guide bar B3 being threaded with third yarns of a biocompatible material, said knitted structure being produced on a determined length along a warp direction corresponding to a total number of N stitches ranging from 1 to N completed along said warp direction by the machine, N being an integer above 7, wherein
   i) a first knit portion is produced along stitches ranging from 1 to x, where 1<x<N, in which the first, the second and the third guide bars (B1, B2, B3) follow a first knit pattern to produce an openworked knit capable of favoring cellular growth,
   ii) a second knit portion is produced for stitches ranging from (x+1) to N, in which the first, the second and the third guide bars (B1, B2, B3) follow a second knit pattern wherein said second and third guide bars B2, B3 produce chain stitches and the first guide bar B1 produces at least a partial weft in which said first yarns complete weft stitches with at least one of said chain stitches, thereby producing at least one weft stitched chain stitch,
b) cutting the second knit portion along the warp direction on both sides of said at least one weft stitched chain stitch and along an edge separating the second knit portion from the first knit portion, so as to remove the second knit portion from the knitted structure while maintaining said weft stitched chain stitch attached to the first knit portion,
wherein the first knit portion forms the mesh and the second or third yarn forming part of said at least one weft stitched chain stitch forms said elongate body of said barbed suture attached thereto, the first yarns cuts extending from said weft stitches of said at least one weft stitched chain stitch forming said barbs of said barbed suture.

2. The method of claim 1, wherein the second knitting pattern followed by the first guide bar B1 during step a)ii) produces at least a partial weft in which said first yarns complete weft stitches with a plurality of chain stitches, thereby producing a plurality of weft stitched chain stitches, and wherein the cutting of step b) is repeated for each weft stitched chain stitch, thereby producing a plurality of barbed sutures attached to the first knit portion.

3. The method of claim 1, wherein said elongate body of said barbed suture is formed of second yarns only.

4. The method of claim 1, wherein the warp knitting machine comprises two needle-beds, a first needle-bed comprising said first, second and third guide bars (B1, B2, B3), and a second needle-bed comprising fourth guide bar B4, fifth guide bar B5 and sixth guide bar B6, said fourth guide bar B4 being threaded with fourth yarns of a biocompatible material, said fifth guide bar B5 being threaded with fifth yarns of a biocompatible material, said sixth guide bar B6 being threaded with sixth yarns of a biocompatible material,
wherein step a) comprises a step 0) occurring before step a)i) as follows:
0) a connecting knit portion is produced along stitches ranging from 1 to y, where 1<y<x<N, in which first, second, third, fourth, fifth and sixth guide bars (B1, B2, B3, B4, B5, B6) produce a three-dimensional openworked knit capable of favoring cellular growth, said knit having a first face produced on said first needle-bed by said first, second and third yarns from said first, second and third guide bars (B1, B2, B3), and a second face, produced on said second needle-bed by said fourth, fifth and sixth yarns from said fourth, fifth and sixth guide bars (B4, B5, B6), said first and second faces being linked together by some of the second, third, fourth and/or fifth yarns, thereby forming linking yarns,
and, in step i), the first knit portion is produced along stitches ranging from (y+1) to x, in which the first, second and third guide bars (B1, B2, B3) produce on the first needle-bed a first bidimensional openworked knit capable of favoring cellular growth, and in which the fourth, fifth and sixth guide bars (B4, B5, B6) produce on the second needle-bed a second bidimensional openworked knit capable of favoring cellular growth,
said first and second bidimensional openworked knits being independent from each other,
and, in step ii) the second knit portion is produced for stitches ranging from (x+1) to N, in which:
on said first needle-bed, a first needle-bed second knit portion is produced, in which said second and third guide bars (B2, B3) produces chain stitches and the first guide bar B1 produces at least a partial weft in which said first yarns complete weft 5 stitches with at least one of said chain stitches, thereby producing at least one first weft stitched chain stitch,
on said second needle-bed, a second needle-bed second knit portion is produced, in which said fourth and fifth guide bars (B4, B5) produces chain stitches and the sixth guide bar B6 produces at least a partial weft in which said sixth yarns complete weft stitches with at least one of said chain stitches, thereby producing at least one second weft stitched chain stitch,
said first needle-bed second knit portion and said second needle-bed second knit portion being independent from each other
wherein step b) comprises:
cutting the first needle-bed second knit portion along the warp direction on both sides of said at least one first weft stitched chain stitch and along an edge separating the first needle-bed second knit portion from the first bidimensional openworked knit, so as to remove the first needle-bed second knit portion from the knitted structure while maintaining said at least one first weft stitched chain stitch attached to the first bidimensional openworked knit,
cutting the second needle-bed second knit portion along the warp direction on both sides of said at least one second weft stitched chain stitch and along an edge separating the second needle-bed second knit portion from the second bidimensional openworked knit, so as to remove the second needle-bed second knit portion from the knitted structure while maintaining said at least one second weft stitched chain stitch attached to the second bidimensional openworked knit,
wherein the method further comprises the following steps occurring after step b°):
c° optionally cutting said linking yarns from the three-dimensional openworked knit obtained in step a)0) along stitches ranging from 2 to y, and
d°) opening the knitted structure so as to spread in a single plane the part of the knitted structure obtained from the first needle-bed and the part of the knitted structure obtained from the second needle-bed,
wherein the first bidimensional openworked knit, the connecting knit portion, optionally cut according to step c°), and the second bidimensional openworked knit form altogether the mesh; the second or third yarn forming part of said at least one first weft stitched chain stitch forms the elongate body of a first barbed suture attached to the first bidimensional openworked knit, the first yarns cuts extending from said weft stitches of said at least one first weft stitched chain stitch forming said barbs of said first barbed suture; the fourth or fifth yarn forming part of said at least one second weft stitched chain stitch forms the elongate body of a second barbed suture attached to the second bidimensional openworked knit, the sixth yarns cuts extending from said weft stitches of said at least one second weft stitched chain stitch forming said barbs of said second barbed suture.

5. The method of claim 4, wherein the first guide bar B1 on the first needle-bed, respectively by the sixth guide bar B6 on the second needle-bed, during step a)ii), produces at least a partial weft in which said first yarns, respectively said sixth yarns, complete weft stitches with a plurality of chain stitches, thereby producing a plurality of first and second weft stitched chain stitches, and wherein the cutting of step b) is repeated for each of said first and second weft stitched chain stitches, thereby producing a plurality of first barbed sutures attached to the first bidimensional openworked knit, respectively a plurality of second barbed sutures attached to the second bidimensional openworked knit.

6. The method of claim 4, wherein said elongate body of said second barbed suture is formed of fifth yarns only.

7. The method of claim 1, wherein the first yarns are monofilaments.

8. The method of claim 1, wherein the sixth yarns are monofilaments.

9. The method of claim 1, further comprising a stretching step during which the second knit portion produced in step a)ii) and/or the attached barbed suture obtained in step b°) is submitted to a stretching treatment.

10. The method of claim 1, wherein the attached barbed suture is submitted to a twisting treatment.

11. The method of claim 1, further comprising a heat-setting step during which either the second knit portion produced in step a)ii) or the attached barbed suture resulting from step b) is submitted to a heat-setting treatment.

12. A prosthetic mesh having at least one barbed suture attached thereto, said barbed suture comprising an elongate body made of a yarn of biocompatible material, provided with barbs extending substantially radially out from said elongate body, said barbs being yarns cuts made of a biocompatible material, where said yarns cuts are stitched to said yarn forming said elongate body, said prosthetic mesh being obtained by the method according to claim 1.

13. The method of claim 4, wherein said first and second faces are linked together the third and/or fourth yarns crossing from the first needle-bed to the second needle-bed.

\* \* \* \* \*

UNITED STATES PATENT AND TRADEMARK OFFICE
CERTIFICATE OF CORRECTION

PATENT NO. : 10,682,215 B2
APPLICATION NO. : 15/716979
DATED : June 16, 2020
INVENTOR(S) : Xavier Couderc and Pierre Bailly It is certified that error appears in the above-identified patent and that said Letters Patent is hereby corrected as shown below:

In the Specification

Insert the word, --SUMMARY,--, after Column 3, Line 23, and before Line 24.

Signed and Sealed this
Twenty-sixth Day of August, 2025

Coke Morgan Stewart
*Acting Director of the United States Patent and Trademark Office*